(12) United States Patent
Kobayashi et al.

(10) Patent No.: US 8,897,862 B2
(45) Date of Patent: Nov. 25, 2014

(54) FETAL CARDIAC POTENTIAL SIGNAL EXTRACTION PROGRAM, FETAL CARDIAC POTENTIAL SIGNAL DISCRIMINATING APPARATUS, AND PREGNANCY MONITORING SYSTEM USING THE SAME

(71) Applicants: Public University Corporation Nara Medical University, Nara (JP); Kinki University, Osaka (JP)

(72) Inventors: Hiroshi Kobayashi, Nara (JP); Toshiyuki Sado, Nara (JP); Hisashi Yoshida, Wakayama (JP)

(73) Assignees: Public University Corporation Nara Medical University, Nara (JP); Kinki University, Osaka (JP)

( * ) Notice: Subject to any disclaimer, the term of this patent is extended or adjusted under 35 U.S.C. 154(b) by 0 days.

(21) Appl. No.: 13/951,274

(22) Filed: Jul. 25, 2013

(65) Prior Publication Data
US 2013/0310701 A1 Nov. 21, 2013

Related U.S. Application Data

(63) Continuation of application No. PCT/JP2012/000475, filed on Jan. 25, 2012.

(30) Foreign Application Priority Data

Jan. 25, 2011 (JP) .................................. 2011-012886

(51) Int. Cl.
*A61B 5/04* (2006.01)
*A61B 5/024* (2006.01)
*A61B 5/0444* (2006.01)
*A61B 5/00* (2006.01)

(52) U.S. Cl.
CPC ........... *A61B 5/02411* (2013.01); *A61B 5/0444* (2013.01); *A61B 5/4362* (2013.01); *A61B 5/7235* (2013.01)
USPC ....................................................... 600/511

(58) Field of Classification Search
CPC ............. A61B 5/02411; A61B 5/0444; A61B 5/4362; A61B 5/7235
USPC .......................................................... 600/511
See application file for complete search history.

(56) References Cited

U.S. PATENT DOCUMENTS 5,372,139 A * 12/1994 Holls et al. ..................... 600/511
8,064,991 B2  11/2011 Hersh et al.

FOREIGN PATENT DOCUMENTS

JP  54-22986 A  2/1979
(Continued)

OTHER PUBLICATIONS

Ishikawa et al, "The Fetal Electrocardiogram by Independent Component Analysis and Wavelets," Therapeutic Research, 2004, pp. 401-404, vol. 25, No. 2.
(Continued)

*Primary Examiner* — George Manuel
(74) *Attorney, Agent, or Firm* — Muncy, Geissler, Olds & Lowe, P.C.

(57) ABSTRACT

A non-transitory computer-readable recording medium storing a computer program, the computer program comprising: a selecting module configured to select, from among a plurality of biopotential signals, a biopotential signal containing a high proportion of a maternal cardiac potential signal component; an independent component analysis module configured to perform independent component analysis on the plurality of biopotential signals; a periodic signal detection module configured to detect, as a first peak time signal, a signal having periodic peaks from a biopotential signal and to detect, as second peak time signals, one or more signals having periodic peaks among signals output from the independent component analysis module; and an output signal selecting module configured to select from among the one or more second peak time signals a signal having peak times different from those of the first peak time signal.

7 Claims, 20 Drawing Sheets

(56) References Cited

FOREIGN PATENT DOCUMENTS

| JP | 2005-503883 A | 2/2005 |
| JP | 2006-204759 A | 5/2006 |
| JP | 2009-160410 A | 7/2009 |
| WO | WO 2006/080167 A1 | 2/1979 |
| WO | WO 03/028550 A2 | 4/2003 |

OTHER PUBLICATIONS

International Preliminary Report on Patentability issued on Jul. 30, 2013, in corresponding International Patent Application No. PCT/JP2012/000475, and an English language translation thereof.
International Search Report issued on Mar. 12, 2012, in corresponding International Patent Application No. PCT/JP2012/000475, and an English language translation thereof.

* cited by examiner

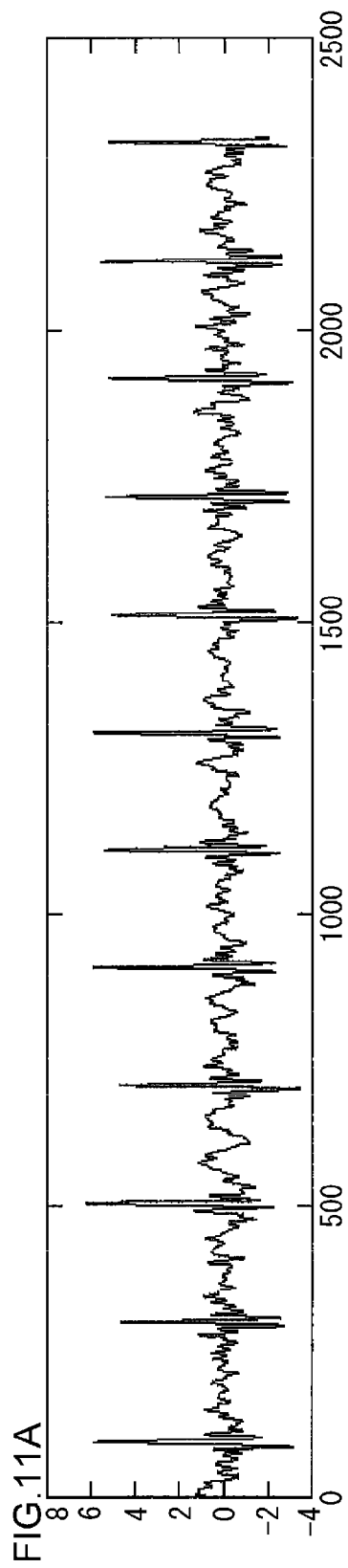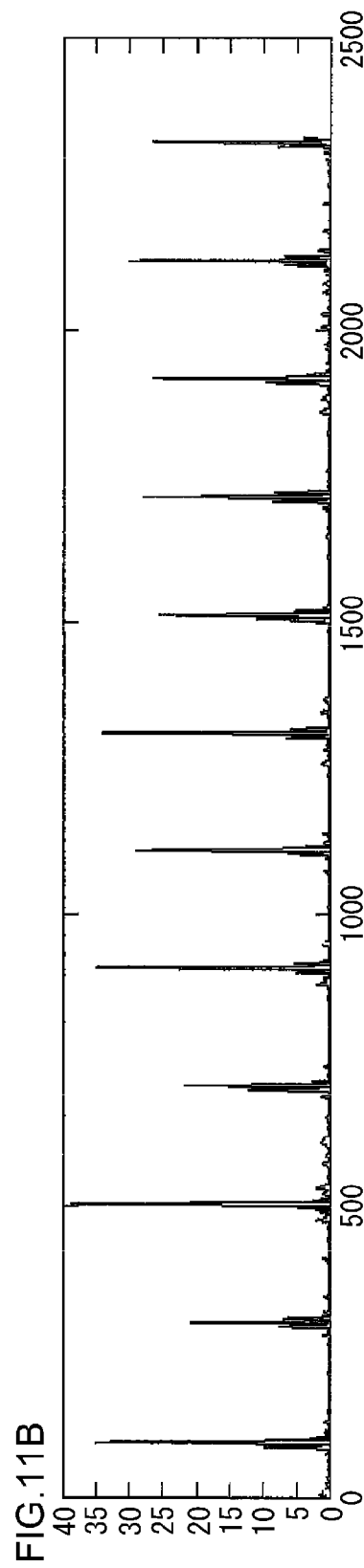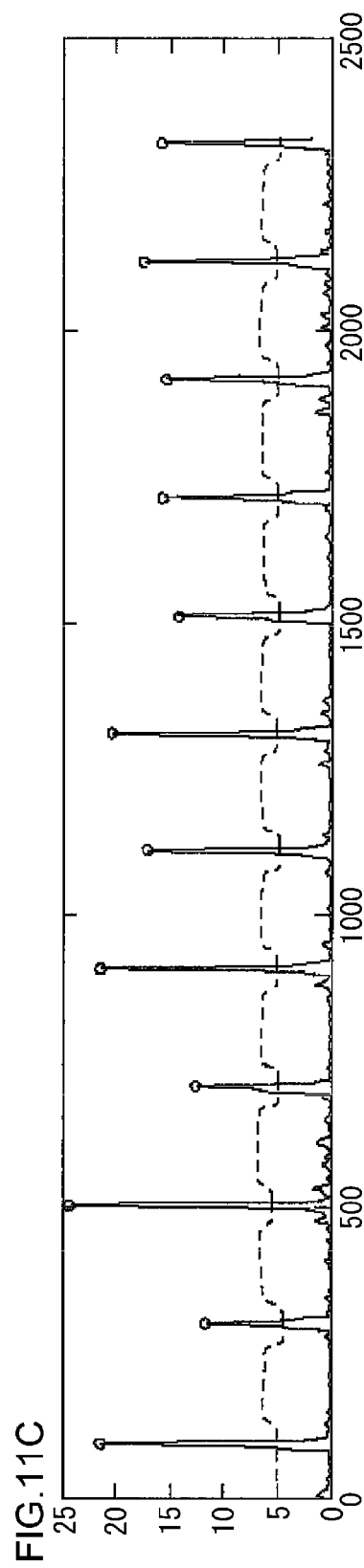

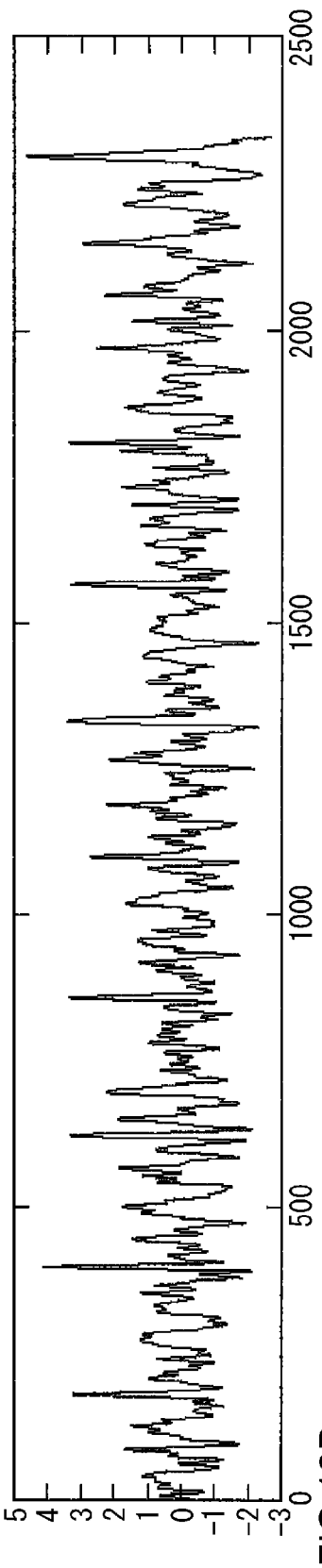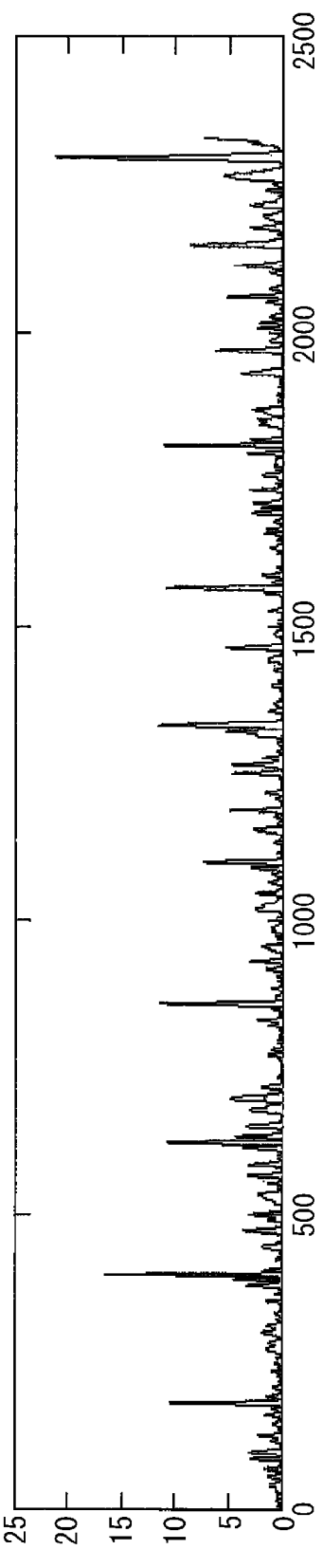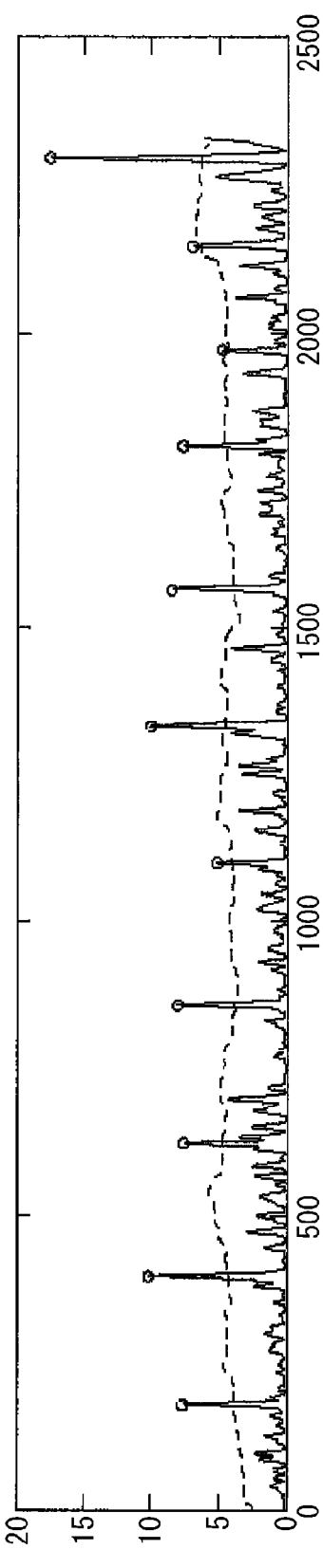

FETAL CARDIAC POTENTIAL SIGNAL EXTRACTION PROGRAM, FETAL CARDIAC POTENTIAL SIGNAL DISCRIMINATING APPARATUS, AND PREGNANCY MONITORING SYSTEM USING THE SAME

BACKGROUND OF THE INVENTION

1. Field of the Invention

The present invention relates to an apparatus and a method for discriminating and acquiring a potential signal that represents the heart rate of a fetus, non-invasively (without pain or danger) from the body of a pregnant woman.

2. Description of the Related Art

If a signal representing the heart rate of a fetus or even the electrocardiogram of a fetus can be detected from the body of a pregnant woman, the health conditions of the fetus can be monitored. This also enables early detection of a situation where premature birth is likely to occur, for example. However, since fetal signals are extremely weak, detecting such signals upon the mother's body is not easy. Noise from the measuring instrument or external noise makes the detection more difficult. Furthermore, since fetal signals detected upon the mother's abdomen are mixed with maternal signals, it is difficult to sharply distinguish the fetal signals.

There have been proposed methods and apparatuses for extracting a fetal electrocardiogram signal while eliminating such difficulties (see Patent Document 1, for example). In the method and apparatus, an ultrasonic sensor for detecting a period of fetal heartbeats is provided upon a mother's body, and a reference signal is generated based on the output from the ultrasonic sensor. Also, electrodes are placed upon the abdomen and chest of the mother so as to detect biopotential signals. Accordingly, a fetal electrocardiogram signal is extracted from the biopotential signals based on the reference signal.

As an apparatus for measuring the heart rate of a fetus, though not the electrocardiogram thereof, a measuring apparatus adopting the ultrasonic Doppler method is generally used. Such a measuring apparatus is configured to emit ultrasonic waves from a probe placed upon the maternal abdomen so as to measure the fetal heart rate using the Doppler effect.

Also, there has been disclosed the technique of identifying the heart rate of a fetus by performing independent component analysis on biopotential data measured on the abdomen of a pregnant woman (see Patent Document 2). In the technique disclosed in Patent Document 2, an operator selects a fetal cardiac potential signal from among multiple independent signals obtained by performing independent component analysis on cardiac potential data, with reference to the percentage of the total energy found in each independent signal.

Further, there has been proposed another technique of performing independent component analysis on biopotential data measured on the abdomen of a pregnant woman so as to identify the maternal heart rate and fetal heart rate according to the frequency range of the heart rate or according to the correlation between the heart rate and a template of a fetal cardiac potential pattern or a template of a maternal cardiac potential pattern (see Patent Document 3).

[Patent Document 1]
JP 2006-204759 A
[Patent Document 2]
Published Japanese Translation of PCT Application No. 2005-503883 A
[Patent Document 3]
JP 2009-160410 A In the method and apparatus for extracting a fetal electrocardiogram signal using ultrasonic as described above, electrodes need be placed upon the abdomen and chest of a pregnant woman, and an ultrasonic sensor is also required. Further, processing for generating a reference signal based on the output from the ultrasonic sensor need also be performed. Accordingly, the apparatus becomes complicated as a whole, and it takes experience to place the electrodes or ultrasonic sensor. Namely, such an apparatus is unable to be used outside medical institutions.

Meanwhile, in the measuring apparatus adopting the ultrasonic Doppler method, the heart rate cannot be measured unless ultrasonic waves are provided to the front of the fetal heart so as to receive the reflected waves. Especially, around the fifteenth week of pregnancy, the fetus, whose heart is very small, may move around in amniotic fluid, making the measurement more difficult. Accordingly, it cannot be said that the heart rate can be certainly measured.

With regard to the technique in which an operator selects a fetal signal from among multiple independent signals obtained by performing independent component analysis on cardiac potential data, a pregnant woman cannot, for example, casually measure and check the fetal cardiac potential at home using the technique. Although Patent Document 2 states that the selection of a fetal cardiac potential signal can be automated, the specific principle thereof is not disclosed.

Further, with regard to the technique of identifying maternal cardiac potential and fetal cardiac potential through frequency analysis, since especially the cardiac potential data of a fetus is extremely weak and susceptible to noise, specifying a dominant frequency within the frequency range is not always easy.

Considering that fetal cardiac potential data is extremely weak, the inventors of the subject application have recognized the possibility of identification of maternal cardiac potential and fetal cardiac potential by utilizing the fact that a biopotential signal measured on the maternal abdomen contains a large proportion of the maternal cardiac potential signal component.

SUMMARY OF THE INVENTION

In view of such conventional problems, a purpose of the present invention is to provide an apparatus and a method for detecting a fetal cardiac potential signal simply and certainly.

To accomplish the purpose above, one embodiment of the present invention is a fetal cardiac potential signal extraction program. The program is a computer program comprising: a selecting module configured to select, from among a plurality of biopotential signals, a biopotential signal containing a high proportion of a maternal cardiac potential signal component; an independent component analysis module configured to perform independent component analysis on a plurality of biopotential signals; a periodic signal detection module configured to detect a signal having periodic peaks among a biopotential signal selected by the selecting module and output signals after independent component analysis, as a peak time signal; an output signal selecting module configured to acquire, as reference input, a biopotential signal that is selected by the selecting module and detected as a peak time signal and also acquire, as comparison input, a peak time signal among output signals after independent component analysis, so as to select an output signal having peak times different from those of the biopotential signal detected as a peak time signal; and a module configured to output a selected output signal.

To accomplish the purpose above, another embodiment of the present invention is a pregnancy monitoring system. The system comprises: a maternity girdle having a plurality of electrodes provided thereon for acquiring a plurality of biopotential signals derived from both a mother and a fetus; and a portable information processor configured to perform the aforementioned program and capable of being carried by a pregnant woman wearing the maternity girdle. The portable information processor displays an output signal selected by the output signal selecting module.

To accomplish the purpose above, yet another embodiment of the present invention is also a pregnancy monitoring system. The system comprises: a maternity girdle having a plurality of electrodes provided thereon for acquiring a plurality of biopotential signals derived from both a mother and a fetus; an information processor configured to perform the aforementioned program and installed in the house of a pregnant woman wearing the maternity girdle; and a server connected to the information processor via a communication line.

To accomplish the purpose above, a further embodiment of the present invention is a fetal cardiac potential signal discriminating apparatus. The apparatus comprises: a measuring apparatus configured to acquire, from a plurality of electrodes placed on the body of a pregnant woman, biopotential signals derived from both a mother and a fetus; and an information processor configured to detect a period of a maternal cardiac potential signal from the waveforms of the biopotential signals, perform independent component analysis on the biopotential signals to acquire a plurality of potential signals having periods different from each other, compare the periods of the plurality of potential signals with the period of the maternal cardiac potential signal, and identify a potential signal having a greatly different period as a fetal cardiac potential signal.

BRIEF DESCRIPTION OF THE DRAWINGS

Embodiments will now be described, by way of example only, with reference to the accompanying drawings which are meant to be exemplary, not limiting, and wherein like elements are numbered alike in several Figures, in which:

FIGS. 11A-11C are diagrams used to describe threshold determination performed by a threshold control module;

FIGS. 12A-12C are other diagrams used to describe threshold determination performed by the threshold control module;

DETAILED DESCRIPTION OF THE INVENTION

The invention will now be described by reference to the preferred embodiments. This does not intend to limit the scope of the present invention, but to exemplify the invention.

In the following, a fetal cardiac potential signal discriminating apparatus according to an embodiment of the present invention will be described with reference to the drawings.

<<Electrode Arrangement>>

Figure 1:
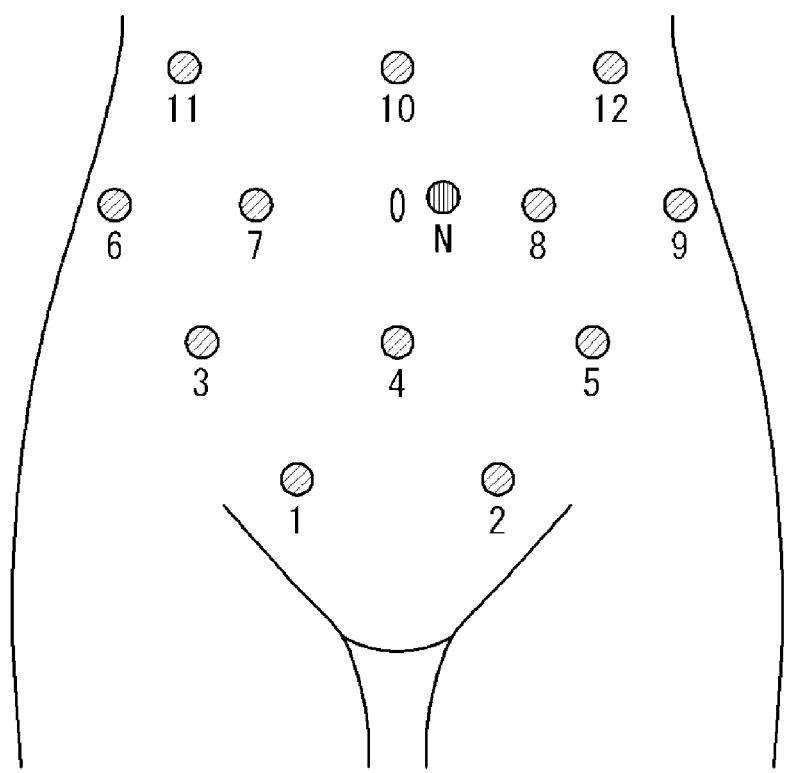
FIG. 1 is a diagram that shows a typical example of electrode arrangement on the abdomen of a pregnant woman, with a measuring apparatus included in a fetal cardiac potential signal discriminating apparatus according to an embodiment of the present invention.
Figure 2:
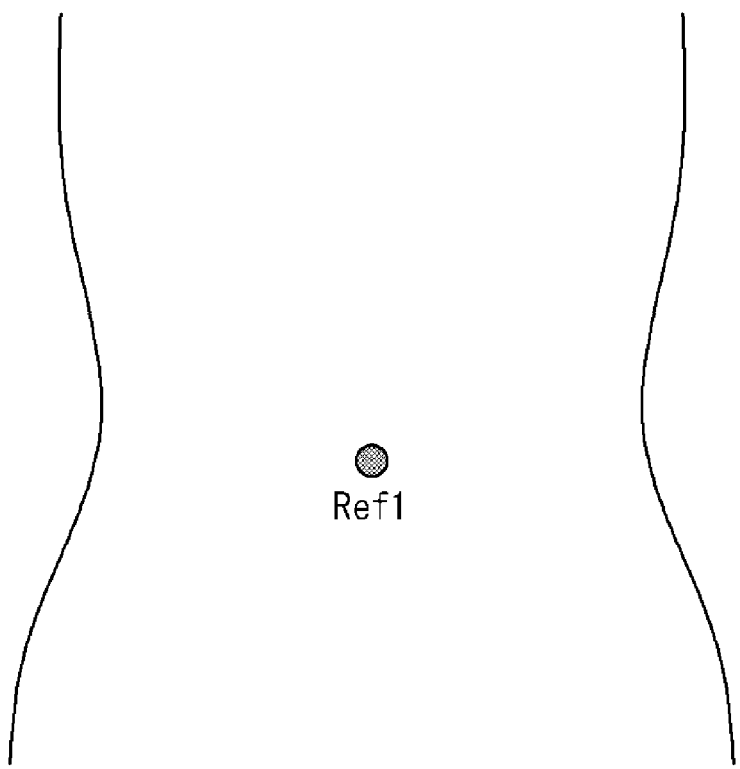
FIG. 2 is a diagram that shows a typical example of electrode arrangement on the back (lumbar region) of a pregnant woman, with a measuring apparatus included in a fetal cardiac potential signal discriminating apparatus according to an embodiment of the present invention.

FIGS. 1 and 2 show typical examples of electrode arrangement on the abdomen and the back (lumbar region) of a pregnant woman, with a measuring apparatus included in a fetal cardiac potential signal discriminating apparatus. In FIG. 1, electrodes 1-12 are arranged over the entire abdomen, and a neutral electrode N is provided beside the navel. Similarly, a reference electrode Ref1 is provided on the back side of the abdomen (lower back) in FIG. 2. Hereinafter, the electrodes 1-12, neutral electrode N, and reference electrode Ref1 may be collectively referred to as electrodes P.

Figure 3:
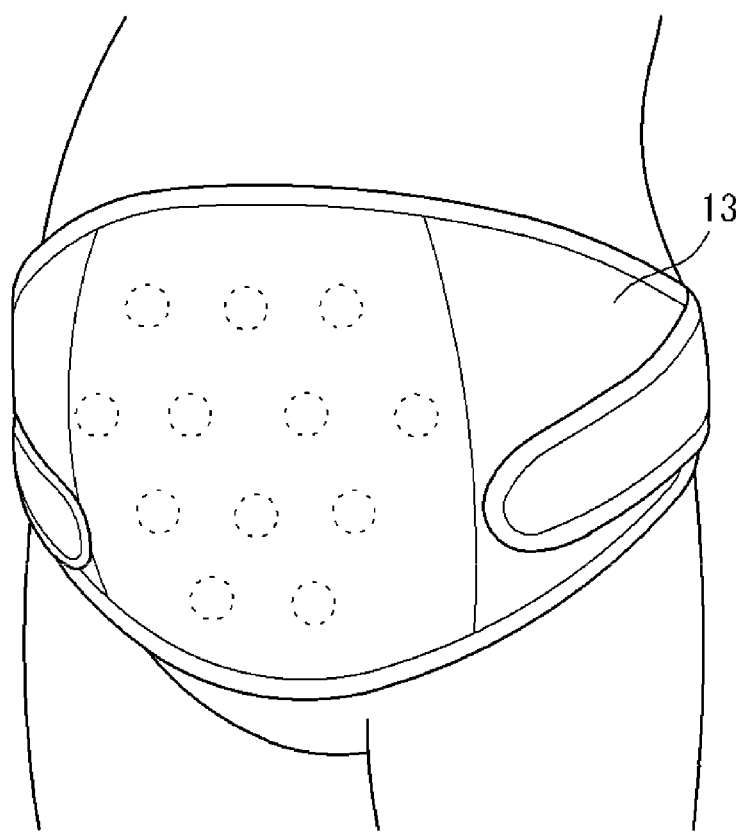
FIG. 3 is a perspective view that shows a state where a maternity girdle is worn around the abdomen of a pregnant woman to simply implement the electrode arrangement.

FIG. 3 is a perspective view that shows a state where a maternity girdle 13 is worn around the abdomen of a pregnant woman to simply implement the electrode arrangement as described above.

On the back side of the front part (the portion in contact with the abdomen) of the maternity girdle 13, necessary electrodes are provided so as to be exposed. When a pregnant woman wears the maternity girdle 13 around her abdomen, the electrodes 1-12, neutral electrode N, and reference electrode Ref1 are firmly attached to certain regions according to the arrangement as shown in FIGS. 1 and 2. Accordingly, a pregnant woman can easily place the electrodes without someone's help.

Figure 4:
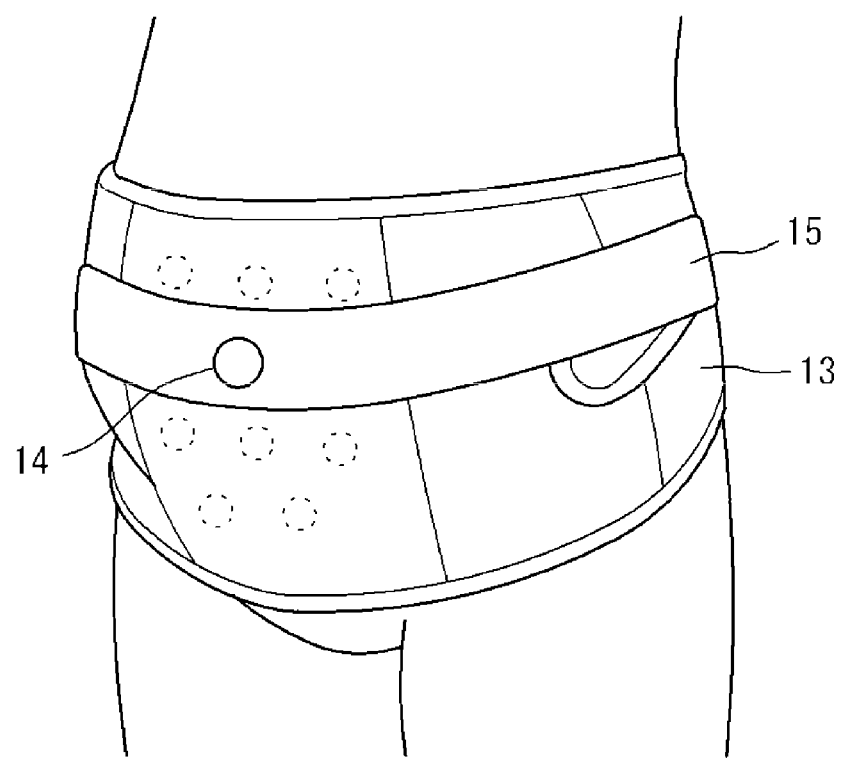
FIG. 4 is a perspective view that shows a state where a belt is worn over the maternity girdle.

FIG. 4 is a perspective view that shows a state where a belt 15 is worn over the maternity girdle 13. To the belt 15 is attached a uterine contraction pressure sensor 14, which detects uterine contraction pressure.

Figure 5:
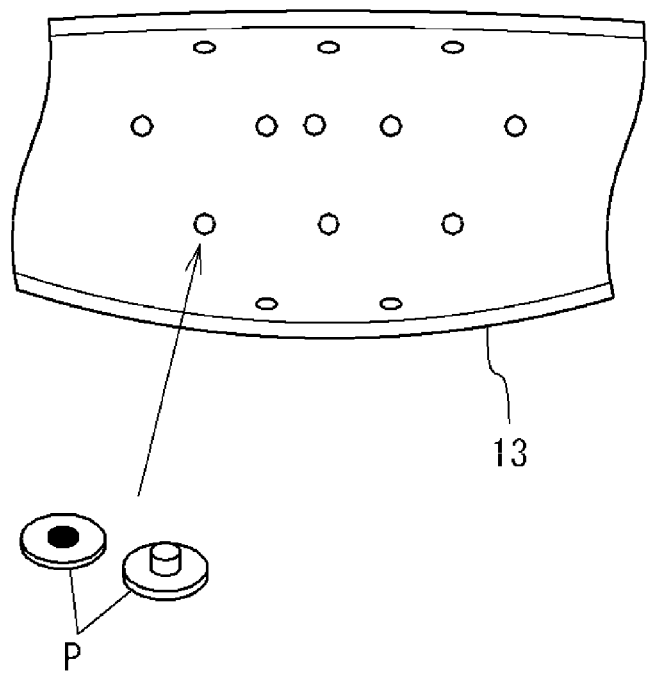
FIG. 5 is a diagram that shows part of the back side of the front part of the maternity girdle.

FIG. 5 shows part of the back side of the front part (abdomen side) of the maternity girdle 13. For the electrodes P, metal button electrodes or pad electrodes, which repeatedly exhibit adhesion, may be used, for example.

Also, the electrodes P and uterine contraction pressure sensor 14 are provided with leads for connecting to an amplifier circuit, though the illustration thereof is omitted.

Figure 6:
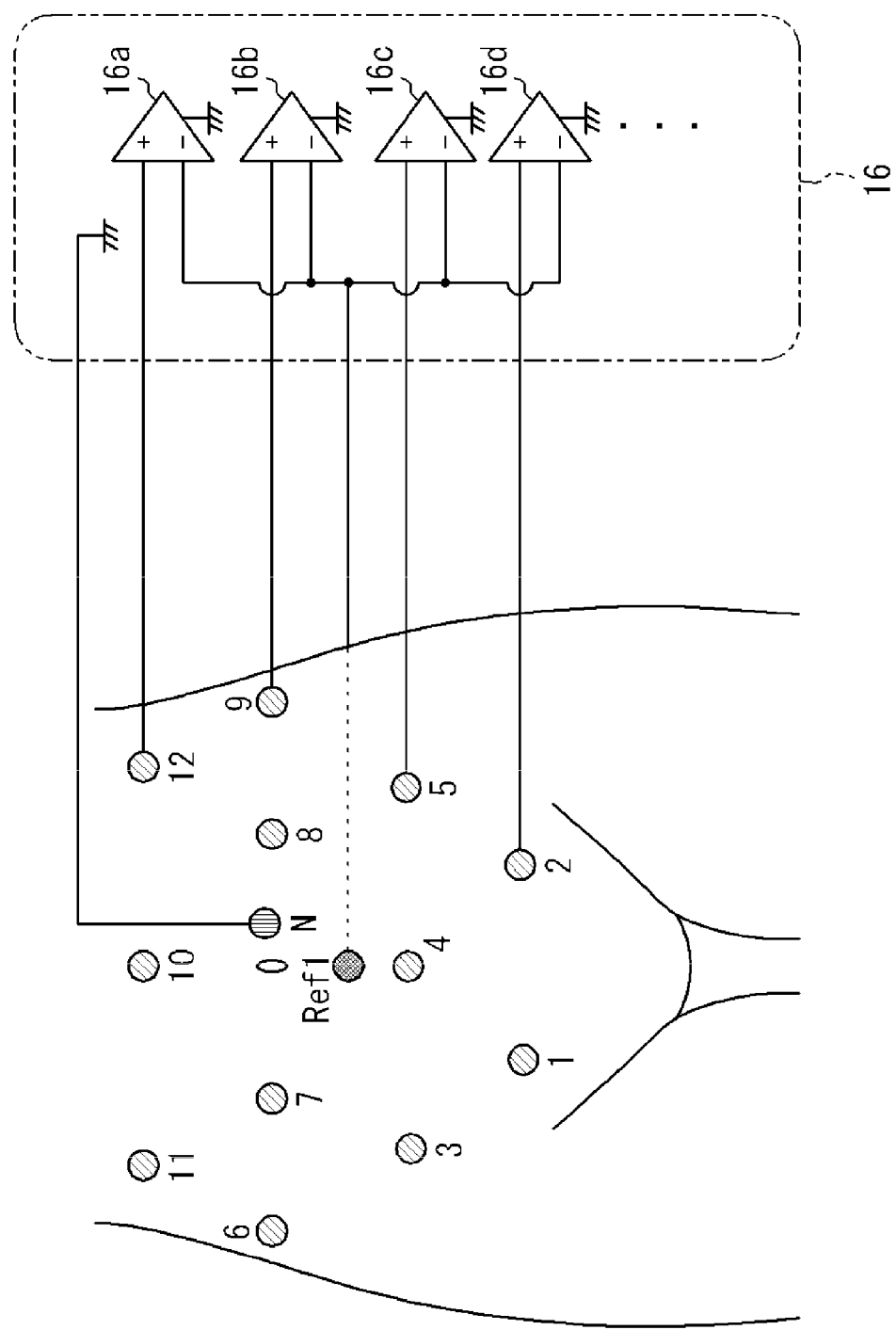
FIG. 6 is a diagram that shows an example of part of circuit connection from the electrodes to amplifiers.

FIG. 6 shows an example of part of circuit connection from the electrodes to amplifiers. Potential signals detected by the electrodes 1-12 are input to the non-inverting input terminals of operational amplifiers 16a, 16b, 16c, 16d . . . (only the four operational amplifiers out of a total of twelve operational amplifiers are shown in FIG. 6) within an amplifier circuit 16 so as to be amplified. A signal from the reference electrode Ref1 is input to the inverting input terminal of each operational amplifier. The neutral electrode N is connected to the ground, in the same way as each operational amplifier.

<<Overall System Configuration>>

Figure 7:
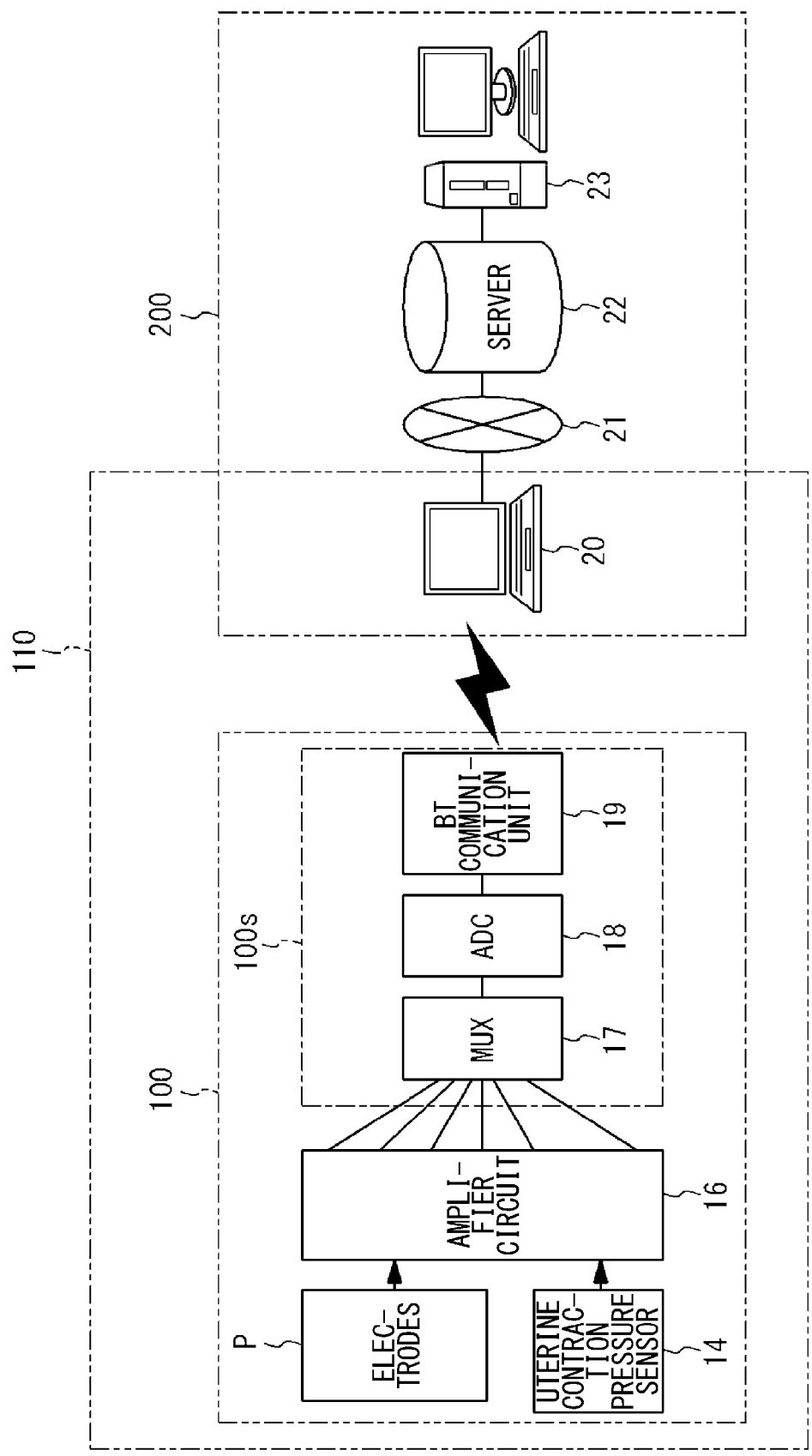
FIG. 7 is a block diagram that shows a measuring apparatus configured with a number of electrodes, an amplifier circuit, and other components and that also shows an information processing system configured to perform information processing based on the output from the measuring apparatus.

FIG. 7 is a block diagram that shows a measuring apparatus 100 configured with a number of electrodes P, the amplifier circuit 16, and other components as described above and that also shows an information processing system 200 configured to perform information processing based on the output from the measuring apparatus 100. The entire system forms a pregnancy monitoring system employing a fetal cardiac potential signal discriminating apparatus 110.

The electrodes P and uterine contraction pressure sensor 14 in the measuring apparatus 100 are provided on the maternity girdle 13 or the like (the maternity girdle 13, belt 15), as described previously. The other part of the measuring apparatus 100, i.e., the amplifier circuit 16 and a transmission unit 100s, is an electronic circuit unit connected to the electrodes P and the uterine contraction pressure sensor 14 and can be compactly configured including a power supply, such as a lithium-ion battery. Accordingly, the electronic circuit unit may be worn as an adjunct to the maternity girdle 13 or the like. Alternatively, the electronic circuit unit may be provided as an external unit connected to the maternity girdle 13 or the like via a lead and placed on the clothes to be carried, similarly to a Holter monitor.

The measuring apparatus 100 and a personal computer (PC) 20 as an information processor constitute the fetal cardiac potential signal discriminating apparatus 110. The PC 20 is installed in a pregnant woman's house. Namely, the fetal cardiac potential signal discriminating apparatus 110 is placed on the body of a pregnant woman or installed in her house. Since the measuring apparatus 100 and the PC 20 communicate with each other wirelessly (via Bluetooth, WiFi, or UWB, for example), the movement of the pregnant woman is not restricted thereby. However, in order to form the fetal cardiac potential signal discriminating apparatus 110, it is necessary that the measuring apparatus 100, i.e., a pregnant woman, is present within a range where wireless communication with the PC 20 is possible. Wireless communication is a preferable example, but the means is not limited thereto. For example, a configuration in which a pregnant woman comes close to the PC 20 so as to connect the measuring apparatus 100 to the PC 20 by wired means (such as a USB) is also available.

To the amplifier circuit 16 of the measuring apparatus 100 in FIG. 7, signals from a number of electrodes P and a signal from the uterine contraction pressure sensor 14, as needed, are input to be amplified. Signals from the electrodes P are biopotential signals derived from both the mother and the fetus. The biopotential signals thus amplified are converted into digital signals by an A/D converter 18 via a multiplexer 17. Such digital signals are then transmitted from a Bluetooth communication unit 19 to the PC 20. The PC 20 has the role of, in a manner, an electronic maternal and child health handbook for gathering maternal or fetal information.

The multiplexer 17, A/D converter 18, and Bluetooth communication unit 19 constitute the transmission unit 100s.

Thus, the measuring apparatus 100 is configured to have the electrodes P and amplifier circuit 16 as the main part, with the uterine contraction pressure sensor 14, as needed, and further include the transmission unit 100s for short range communication with the PC 20.

The PC 20 is connected to a server 22 in a medical institution via an Internet connection 21. The server 22 is also connected to a PC 23 for doctors. In the server 22, contact information (such as an e-mail address for a cellular phone) of a pregnant woman or a doctor is registered, so as to be able to contact the pregnant woman or the doctor via the server 22, as needed.

<<Functional Configuration for Fetal Cardiac Potential Signal Discrimination>>

Figure 8:
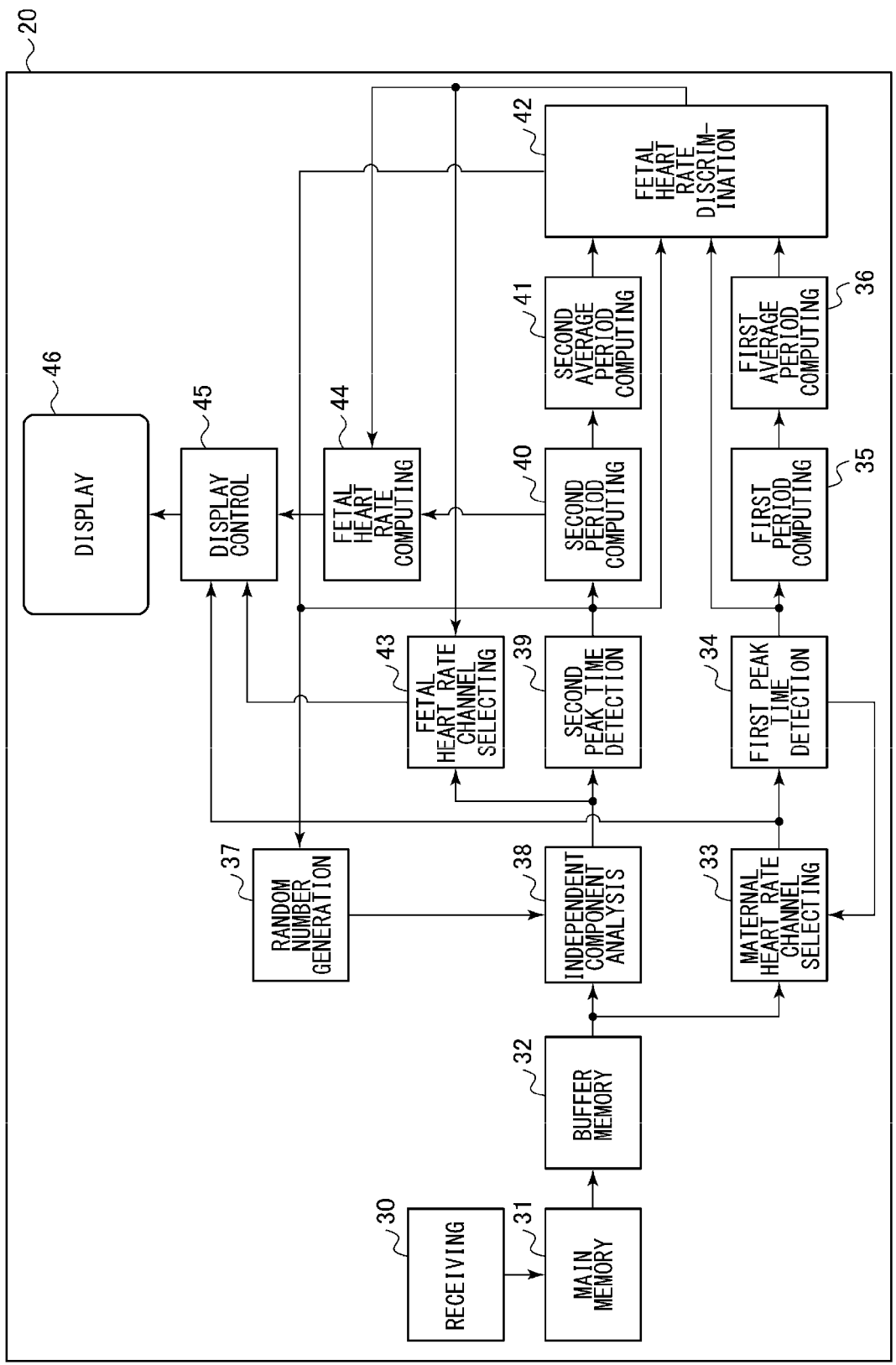
FIG. 8 is a diagram that schematically shows a functional configuration for the discrimination of a fetal cardiac potential signal, including hardware modules of a personal computer and program modules performed by a personal computer to acquire a fetal cardiac potential signal.

FIG. 8 schematically shows a functional configuration for the discrimination of a fetal cardiac potential signal, including hardware modules of the PC 20 and program modules performed by the PC 20 to acquire a fetal cardiac potential signal.

A receiving module 30 is a module to receive biopotential signals transmitted from the measuring apparatus 100. The receiving module 30 may be implemented by a Bluetooth (registered trademark) receiver module and a driver program therefor, for example. Main memory 31 stores biopotential signals received by the receiving module 30.

A buffer memory 32 acquires, every five seconds, data for five seconds of the same period in each of biopotential signals from 12 channels stored in the main memory 31 and stores the acquired data as data for one frame. A maternal heart rate channel selecting module 33 is a module to select from among biopotential signals transmitted from the measuring apparatus 100 a biopotential signal from a channel that is likely to include a maternal heart rate signal and a high proportion of a maternal cardiac potential signal component. When any peak time cannot be detected for the selected channel by a first peak time detection module 34, which will be described later, the maternal heart rate channel selecting module 33 selects another channel and continues the selection of a biopotential signal until a peak time is detected.

The first peak time detection module 34 is a module to detect a peak time of a biopotential signal from a channel selected by the maternal heart rate channel selecting module 33. The specific principle of peak time detection will be described later. A first period computing module 35 computes each peak interval between peak times detected by the first peak time detection module 34. When the variance of the peak intervals between peak times computed by the first period computing module 35 is a predetermined reference variance value or less, the first peak time detection module 34 judges the output signal having such peak times to be a periodic signal. If any periodicity cannot be found in peak times of an input biopotential signal, the first peak time detection module 34 will allow the maternal heart rate channel selecting module 33 to select another biopotential signal. With regard to the first peak, the first period computing module 35 computes the interval between the peak and the last peak in the previous frame.

Generally, a maternal heart rate signal has greater amplitude than a fetal heart rate signal. Accordingly, it is highly possible that a maternal heart rate signal component notably appears in each of multiple biopotential signals stored in the main memory 31. Therefore, when a biopotential signal having periodic peak times is detected, the first peak time detection module 34 assumes the peak times to be those of a maternal heart rate signal.

A first average period computing module 36 is a module to compute an average value of peak time intervals of a biopotential signal judged to be periodic by the first peak time detection module 34, so as to define the average value as an average period of the signal. A random number generation module 37 is a module to generate an initial value of a separating matrix computed by an independent component analysis module 38, which will be described later. The independent component analysis module 38 is a module to presume a signal source based on disnormality, using inputs of multiple observed signals in which signals generated from multiple independent signal sources are mixed in different proportions. The independent component analysis module 38 also presumes a separating matrix by which multiple observed signals are multiplied so as to generate independent signals.

A second peak time detection module 39 is a module to detect, using signals output from the independent component analysis module 38 as input signals, a peak time of each signal. As with the first peak time detection module 34, the specific principle of peak time detection will be described later. A second period computing module 40 computes each peak interval between peak times detected by the second peak time detection module 39. With regard to the first peak, the second period computing module 40 computes the interval between the peak and the last peak in the previous frame.

As with the first peak time detection module 34, when the variance of the peak intervals between peak times detected by the second peak time detection module 39 is a predetermined reference variance value or less, the second peak time detection module 39 judges the output signal having such peak times to be a periodic signal. A second average period computing module 41 is a module to compute an average value of peak time intervals of a biopotential signal judged to be periodic by the second peak time detection module 39, so as to define the average value as an average period of the signal.

A fetal heart rate discrimination module 42 acquires, as reference input, peak times of a maternal heart rate signal detected by the first peak time detection module 34 and an average period of the maternal heart rate signal acquired by the first average period computing module 36. The fetal heart rate discrimination module 42 also acquires, as comparison input, peak time information of a signal judged to be periodic by the second peak time detection module 39 among independent signals generated by the independent component analysis module 38 and average period information of the signal acquired by the second average period computing module 41.

The fetal heart rate discrimination module 42 compares the average period of the maternal heart rate signal and the average period acquired by the second average period computing module 41 and selects, when the difference between the average periods is a predetermined reference value or more, the independent signal as an output signal having peak times different from those of the maternal heart rate signal. If the difference in average period between the maternal heart rate signal and any signal is less than the predetermined reference value, the fetal heart rate discrimination module 42 will select, when the difference between the phase of a peak time of a signal judged to be periodic by the second peak time detection module 39 and the phase of a peak time of the maternal heart rate signal is a predetermined reference phase difference or more, the signal as an output signal having peak times different from those of the maternal heart rate signal.

If each of the independent signals generated by the independent component analysis module 38 has an average period of peak times and a phase of a peak time similar to those of the maternal heart rate signal, the fetal heart rate discrimination module 42 will determine that the independent component analysis has failed and allow the random number generation module 37 to newly generate an initial value of the separating matrix. If the fetal heart rate discrimination module 42 has selected a signal having peak times different from those of the maternal heart rate signal, the fetal heart rate discrimination module 42 will output, to a display 46 or the like, discrimination information for identifying the channel as a fetal cardiac potential signal. If the discrimination of a fetal heart rate signal cannot be made within five seconds, the fetal heart rate discrimination module 42 will stop the discrimination operation for the frame.

A fetal heart rate channel selecting module 43 is a module to select a fetal heart rate signal from among signals output from the independent component analysis module 38 based on the discrimination information from the fetal heart rate discrimination module 42 and output the signal. A fetal heart rate computing means 44 is a module to compute the heart rate of a fetus using the peak period of a signal selected as a fetal heart rate signal from among signals output from the independent component analysis module 38 based on the discrimination information from the fetal heart rate discrimination module 42.

A display control module 45 is a module to continuously output, to the display 46, at least a biopotential signal in which a maternal heart rate signal component notably appears, a signal judged to be a fetal heart rate signal among signals output from the independent component analysis module 38, and a fetal heart rate computed by the fetal heart rate computing means 44, so as to display, on the display 46 of a personal computer, the maternal heart rate waveform and the fetal heart rate waveform for multiple frames and a graph showing variations in the fetal heart rate. The graph showing fetal heart rate variations is important for a doctor to check the health conditions of a fetus, so that the graph is an essential element to be displayed on a personal computer for doctors. Although a monitor screen on a personal computer is used as the display 46 in the present embodiment, by applying the present embodiment to a mobile terminal with functions equivalent to those of a personal computer, the waveforms or graph can be displayed on the display of a mobile terminal.

Figure 9:
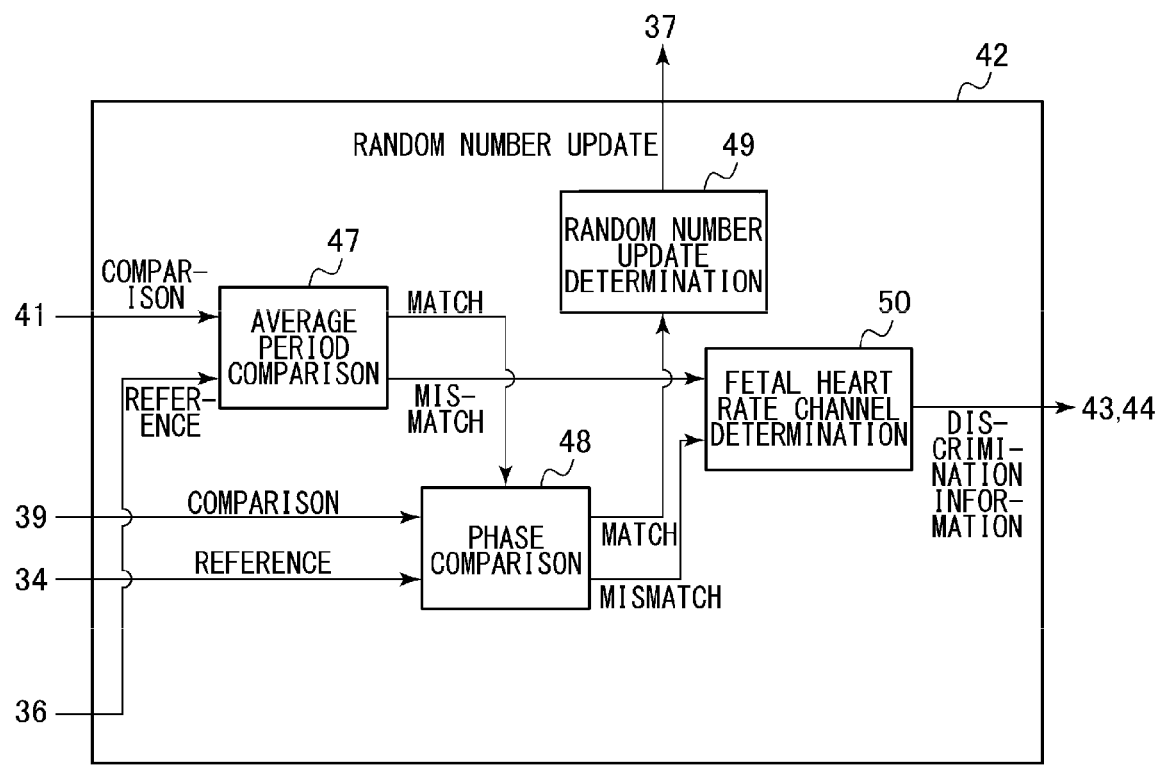
FIG. 9 is a diagram that shows detailed internal modules of a fetal heart rate discrimination module.

FIG. 9 shows detailed internal modules of the fetal heart rate discrimination module 42.

The fetal heart rate discrimination module 42 acquires, as reference input, peak times of a maternal heart rate signal detected by the first peak time detection module 34 and an average period of the maternal heart rate signal acquired by the first average period computing module 36. The fetal heart rate discrimination module 42 also acquires, as comparison input, peak time information of a signal judged to be periodic by the second peak time detection module 39 among independent signals generated by the independent component analysis module 38 and average period information of the signal acquired by the second average period computing module 41. The average period comparison module 47 compares the average period of the maternal heart rate signal and the average period acquired by the second average period computing module 41 and provides, when the difference between the average periods is a predetermined reference value or more, a mismatch output indicating that the peak times of the signal do not coincide with the peak times of the maternal heart rate signal. If the difference between the average periods is less than the predetermined reference value, the average period comparison module 47 will provide a match signal.

When the average period comparison module 47 has provided a match output and if the difference between the phase of a peak time of a signal judged to be periodic by the second peak time detection module 39 and the phase of a peak time of the maternal heart rate signal is a predetermined reference phase difference or more, a phase comparison module 48 will provide a mismatch output. If the difference between the phase of a peak time of any signal judged to be periodic by the second period computing module 40 and the phase of a peak time of the maternal heart rate signal is less than the predetermined reference phase difference, the phase comparison module 48 will determine that there is no independent component data identified as a fetal heart rate signal and will provide a match output.

A random number update determination module 49 receives a match output provided by the phase comparison module 48 and generates a random number update output if it is within one frame period. A fetal heart rate channel determination module 50 receives a mismatch output provided by the average period comparison module 47 and the phase comparison module 48 and generates discrimination information for identifying the channel judged to be a mismatch channel.

Figure 10:
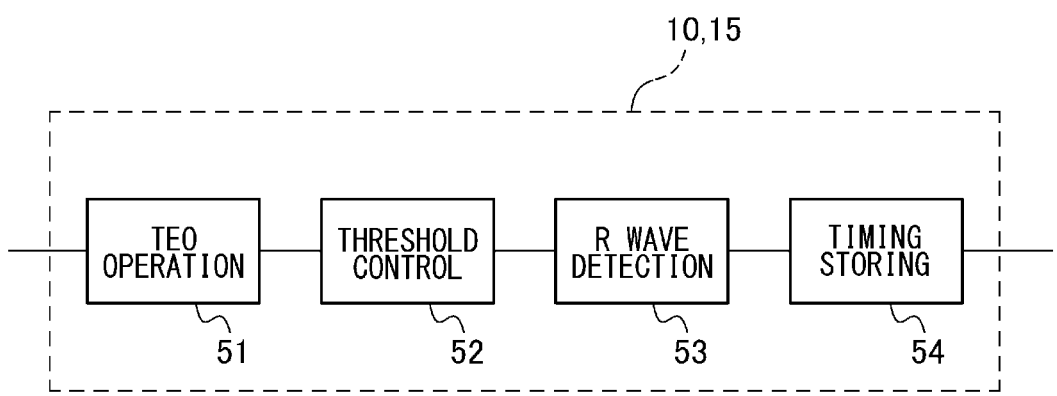
FIG. 10 is a diagram that shows detailed internal modules of a first peak time detection module and a second peak time detection module.

FIG. 10 shows detailed internal modules of the first peak time detection module 34 and the second peak time detection module 39.

A TEO operation module 51 is a Teager energy operation module to generate signal energy by suppressing minute noise. The "signal energy" indicates, for example, the amplitude of the signal at each sampling point, and the Teager energy operation is a means for obtaining such signal energy. Accordingly, a signal obtained by squaring the amplitude at each sampling point, instead of performing the Teager energy operation, also indicates "signal energy". The Teager energy operation is an example of means for computing signal energy, and it would be easily understood by those skilled in the art that an energy operation other than the Teager energy operation may also be used.

The Teager energy operator is known as a means for obtaining time marginal distribution. The square-law detection or cross correlation may be cited as a method for a similar purpose, but the method using the Teager energy operator is significantly effective when the power of a cardiac potential signal is greater than the power of noise; namely, with improved S/N ratio, a cardiac potential signal can be detected more accurately than when the square-law detection or cross correlation is used.

Characteristic components of an electrocardiogram waveform include a P wave, a Q wave, an R wave, an S wave, and a T wave, in which the R wave having a significant peak with a greater value can be easily detected.

A threshold control module 52 is a module to control the level of a threshold so as not to mistakenly detect a peak of noise, by lowering the threshold level for peak detection during a period in which a peak of a heart rate signal is expected and by raising the threshold level during the other periods.

Generally, when a heartbeat interval is to be measured from a cardiac potential signal, the peak of a continuous R wave, which has a waveform including the largest amplitude in a cardiac potential signal, is detected, and an interval between such peaks is measured. If the amount of superimposed noise is relatively low and there is no large variation in the baseline, there may be used the method of determining an appropriate threshold so as to obtain the maximum point among values exceeding the threshold. Since it is simple and requires a less amount of calculation, the method is suitable for real-time processing.

However, since peaks of a separated fetal cardiac potential signal are detected through the maternal abdominal wall in the present embodiment, there can be considered the case where a large amount of noise is mixed into a potential signal to be analyzed or the case where even the amplitude of the signal is changed. In such a case, the method of using a fixed threshold may not be able to be used to precisely detect the peak of an R wave. The threshold control module 52 then uses moving averages of a potential signal to be analyzed so as to set a variable threshold. Accordingly, even if noise is mixed into a potential signal to be analyzed, robust detection of peak times is enabled.

FIG. 11 are diagrams used to describe the threshold determination performed by the threshold control module 52. In each diagram of FIG. 11, the vertical axis represents signal amplitude based on the electric potential detected at each electrode, and the horizontal axis represents the sampling number. In the example shown in each diagram of FIG. 11, the sampling interval is 2 milliseconds. Since the example of each diagram shows data for 2500 samples, it corresponds to data for 5 seconds, or 1 frame.

FIG. 11A shows an example of an independent signal generated by the independent component analysis module 38. Compared to the example shown in FIG. 12A, which will be described later, the signal shown in FIG. 11A is an exemplary signal in which a fetal cardiac potential signal is relatively clearly separated and signals assumed to be continuous R waves can be recognized. Hereinafter, the independent signal shown in FIG. 11A will be described as x(t), which is a function of time t.

FIG. 11B shows an energy signal y(t) of the signal x(t) shown in FIG. 11A. The threshold control module 52 first applies an appropriate energy operator $\psi(\bullet)$ to the signal x(t) so as to obtain an energy signal y(t). The energy operator $\psi(\bullet)$ may be the square operator, for example, and, in such a case, the threshold control module 52 obtains the energy signal y(t) according to Formula (1) below:

$$y(t) = \psi\{x(t)\} = x(t)^2 \quad (1)$$

Next, in order to facilitate the acquisition of the maximum point in the energy signal y(t), the threshold control module 52 obtains a signal z(t) by smoothing the energy signal y(t). A smoothing filter used therefor may be designed as a low-pass filter or a simple moving average filter. Formula (2) below is employed to obtain z(t) using a simple moving average.

[Math. 1]

$$z(t) = \frac{1}{2N+1} \sum_{\tau=-N}^{N} y(t+\tau) \quad (2)$$

In the formula, N is the order of the simple moving average filter.

Subsequently, in order to acquire a variable threshold, the threshold control module 52 obtains a moving average w(t) of the smoothed energy signal z(t) using Formula (3) below.

[Math. 2]

$$w(t) = \frac{1}{2M+1} \sum_{\tau=-M}^{M} z(t+\tau) \quad (3)$$

In the above formula, M is the filter order and defined to meet Formula (4) below, where the average heartbeat interval within a target period is defined as $RR_{ave}$.

$$RR_{ave} < M < 2RR_{ave} \quad (4)$$

Namely, an interval longer than the average heartbeat interval within a target period but shorter than twice the average heartbeat interval is set to the filter order M, which is the window width for obtaining a moving average.

When the data length for one frame in the signal z(t) is defined as L, the threshold control module 52 obtains the standard deviation σ according to Formula (5) below.

[Math. 3]

$$\sigma = \sqrt{\frac{1}{L}\sum_{\tau=1}^{L} \{z(t) - \overline{z(\tau)}\}^2} \quad (5)$$

where $$\overline{z(\tau)} = \frac{1}{L}\sum_{\tau=1}^{L} z(\tau)$$

Finally, the threshold control module 52 obtains a variable threshold mTh according to the definition provided by Formula (6) below:

$$mTh = \alpha z(t) + \beta \sigma \quad (6)$$

In the formula, α and β are parameters used to acquire the variable threshold mTh. Namely, the variable threshold mTh is a linear sum of the smoothed energy signal z(t) and the standard deviation σ. An R wave detection module 53 detects the maximum point within a part of the signal exceeding the variable threshold mTh as the peak of an R wave. The values of α and β may be determined through experiments based on cardiac potential signals.

FIG. 11C shows the smoothed energy signal z(t) of the signal x(t) shown in FIG. 11A, the variable threshold mTh, and the peaks of R waves detected by the R wave detection module 53. In FIG. 11C, the smoothed energy signal z(t) is indicated by a solid line, the variable threshold mTh is indicated by a dotted line, and each of the peaks of R waves detected by the R wave detection module 53 is indicated by "O". In FIG. 11C, for the signal x(t) assumed to be a fetal cardiac potential signal, the peaks of signals assumed to be continuous R waves exceed the variable threshold mTh while the other signal regions fall below the variable threshold mTh, which indicates successful peak detection.

FIG. 12 are other diagrams used to describe the threshold determination performed by the threshold control module 52. As with FIG. 11, the vertical axis represents signal amplitude based on the electric potential detected at each electrode, and the horizontal axis represents the sampling number in each diagram of FIG. 12. The sampling interval in the example shown in each diagram of FIG. 12 is the same as that in the examples shown in FIG. 11, and hence, each diagram of FIG. 12 shows data for one frame. As with FIG. 11A, FIG. 12A shows an example of an independent signal generated by the independent component analysis module 38, but a larger amount of noise components are superimposed thereon compared to the signal shown in FIG. 11A. FIG. 12B shows an energy signal of the signal shown in FIG. 12A. Compared to the signal shown in FIG. 11b, it is found that the signal shown in FIG. 12B also contains peaks derived from noise components, between signals assumed to be continuous R waves.

FIG. 12C shows the smoothed energy signal of the signal shown in FIG. 12A and the variable threshold mTh. As with in FIG. 11C, the smoothed energy signal is indicated by a solid line, the variable threshold mTh is indicated by a dotted line, and each of the peaks of R waves detected by the R wave detection module 53 is indicated by "O". As shown in FIG. 12C, even though noise is superimposed on the original signal, peaks can be successfully detected.

The description now returns to FIG. 10, and the R wave detection module 53 compares input biopotential signal data with the level of a threshold generated by the threshold control module 52 so as to detect timing when an R wave in a heart rate waveform is generated. A timing storing module 54 is a module to store the peak time of a detected R wave. The timing storing module 54 may be implemented by a volatile memory, for example.

Next, there will be described an example of the method for determining α and β for the variable threshold mTh defined by the aforementioned Formula (6).

The threshold control module 52 sets each of α and β to a predetermined initial value so as to obtain an initial value of the variable threshold mTh. The threshold control module 52 then obtains an energy signal and acquires a peak candidate of a signal greater than or equal to the initial value of the variable threshold mTh in the energy signal. Namely, the "predetermined initial value" set by the threshold control module 52 is a reference initial value for peak candidate computation provided to acquire a peak candidate and may be determined through experiments by statistically processing multiple cardiac potential signals.

The timing storing module 54 stores the time of a peak candidate detected by the R wave detection module 53. The threshold control module 52 then acquires each interval between the peak times of peak candidates stored in the timing storing module 54. For this process, the threshold control module 52 itself may compute each interval between the peak times of peak candidates or may acquire the result of computation performed by the first period computing module 35 or second period computing module 40.

Subsequently, the threshold control module 52 changes at least one of the values of α and β so that the acquired intervals between the peak times become equal. More specifically, the threshold control module 52 increases at least one of the values of α and β by a predetermined amount so as to set an updated threshold. The R wave detection module 53 then newly acquires peak candidates based on the updated threshold and allows the timing storing module 54 to store the peak times of the peak candidates.

An R wave is generally a periodic signal. Since each interval between the peak times of actual peaks is less than or equal to the reference variance value used by the first peak time detection module 34 or the second peak time detection module 39 to determine the periodicity, the threshold control module 52 can use the reference variance value to determine whether or not the peak candidate is an actual peak. If the threshold is small, noise components may be mixed into peak candidates. Accordingly, the threshold control module 52 gradually increases at least one of the values of α and β so as to increase the variable threshold mTh. The threshold control module 52 then repeats the above processing until the value of noise components becomes less than or equal to the threshold and each interval between the peak times of peak candidates becomes less than or equal to the reference variance value, so as to update at least one of the values of α and β. When each interval between the peak times of peak candidates becomes less than or equal to the reference variance value, the threshold control module 52 terminates the updating of the threshold, and the peak times stored in the timing storing module 54 at the time are peak times of R waves.

<<Operation of the Fetal Cardiac Potential Signal Discriminating Apparatus>>

There will now be described the operation of the fetal cardiac potential signal discriminating apparatus 110 in detail. The description for the uterine contraction pressure sensor 14 will be omitted, and the operation relating to biopotential signals obtained from the electrodes P will be described.

Figure 13:
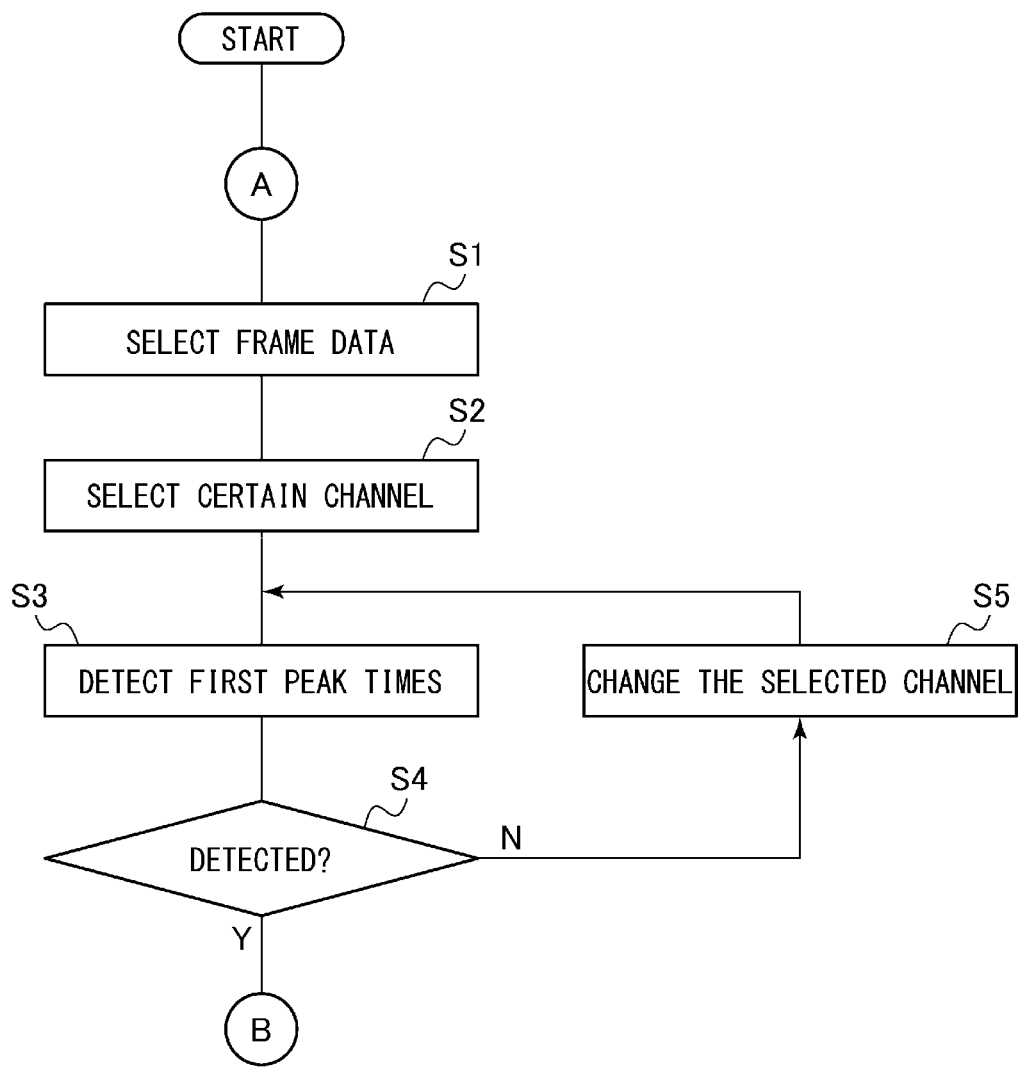
FIG. 13 shows the first part of a flowchart of illustrative processing for discriminating a fetal cardiac potential signal performed by a personal computer.

FIG. 13 shows the first part of a flowchart of illustrative processing for discriminating a fetal cardiac potential signal performed by the PC 20. The buffer memory 32 selects, from the data stored in the main memory 31, frame data to be used for analysis and stores the frame data (S1). The maternal heart rate channel selecting module 33 selects a certain channel from among biopotential signals from 12 channels stored in the buffer memory 32 (S2).

The first peak time detection module 34 detects peak times of a biopotential signal from the channel selected by the maternal heart rate channel selecting module 33 (S3). If peak times cannot be detected successfully (N at S4), the maternal heart rate channel selecting module 33 will select a different channel (S5). If the first peak time detection module 34 has successfully detected peak times (Y at S4), the process will proceed to the step S6 in the middle part of the flowchart shown in FIG. 14.

Figure 14:
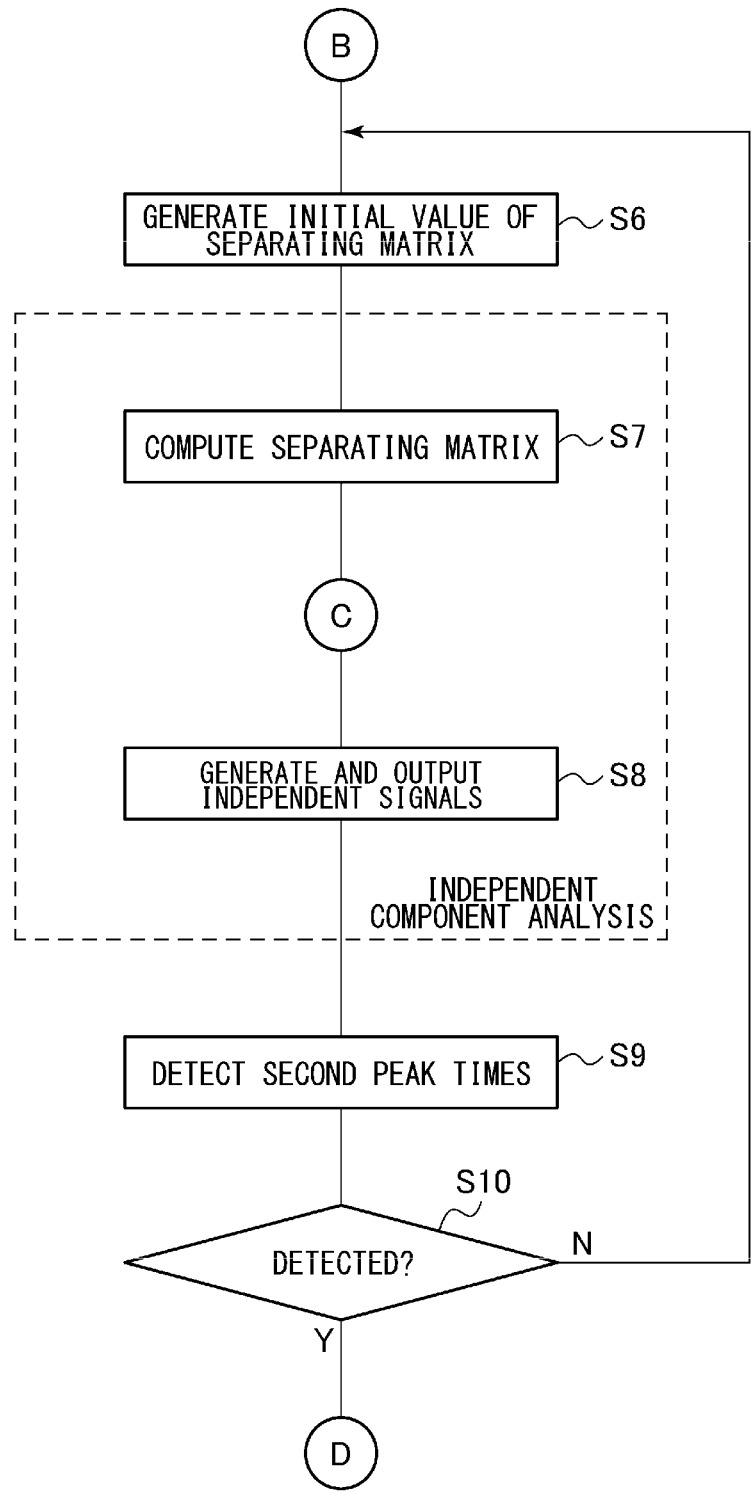
FIG. 14 shows the middle part of the flowchart of illustrative processing for discriminating a fetal cardiac potential signal performed by a personal computer.

FIG. 14 shows the middle part of the flowchart of illustrative processing for discriminating a fetal cardiac potential signal performed by a personal computer.

The random number generation module 37 generates a random number so as to generate an initial value of a separating matrix presumed by the independent component analysis module 38 (S6). Accordingly, the independent component analysis module 38 presumes a separating matrix used to separate the biopotential signals of 12 channels, into which at least a maternal heart rate signal and a fetal heart rate signal are mixed, stored in the buffer memory 32 into independent signals (S7). The independent component analysis module 38 then multiplies the biopotential signals of the 12 channels by the presumed separating matrix so as to generate independent signals and then outputs the generated signals (S8).

The second peak time detection module 39 detects, using signals output from the independent component analysis module 38 as input signals, peak times of each signal (S9). If the second period computing module 40 cannot detect periodicity in peak times detected by the second peak time detection module 39 (N at S10), the process will return to the step S6 and independent component analysis will be started again.

Figure 15:
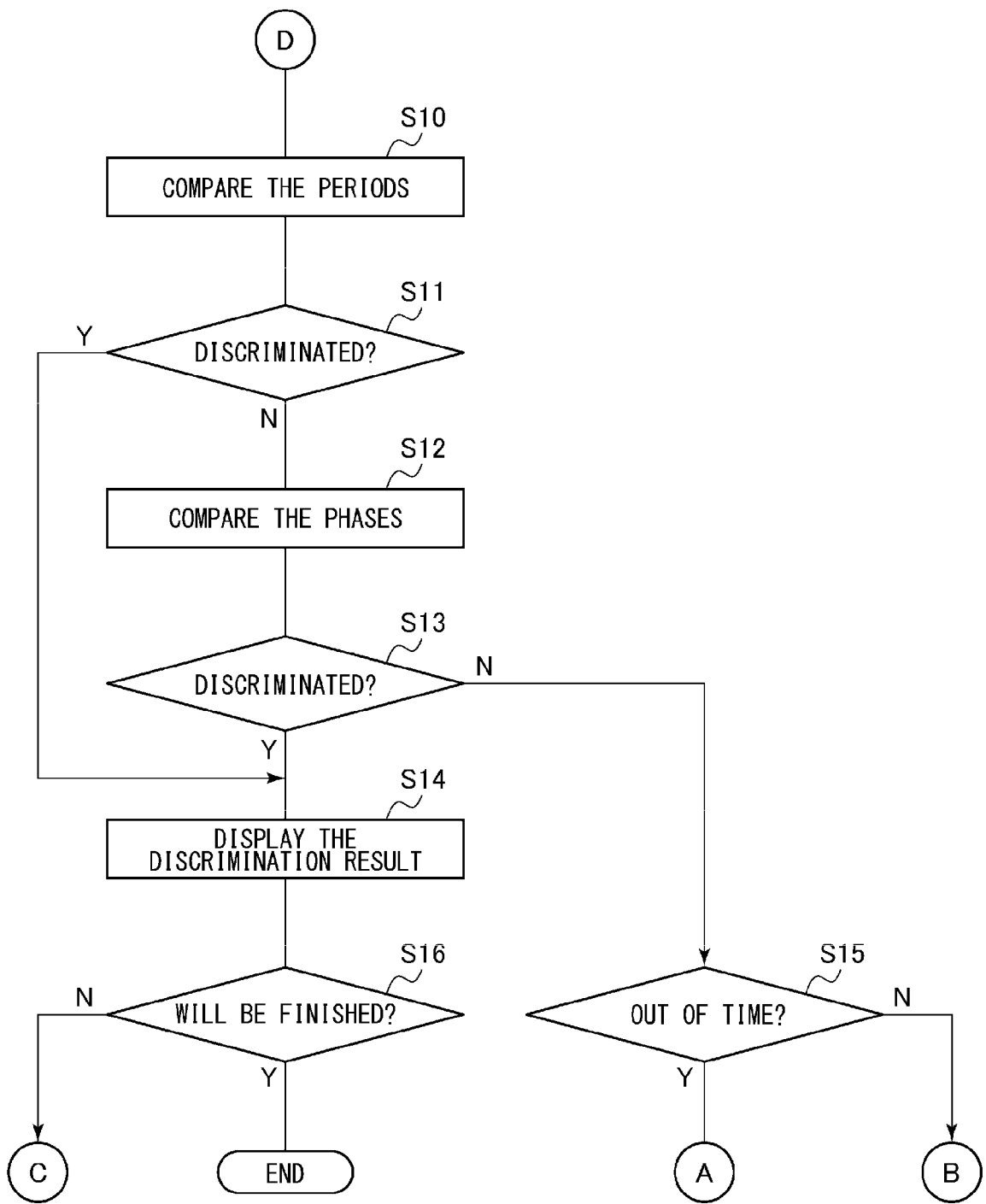
FIG. 15 shows the last part of the flowchart of illustrative processing for discriminating a fetal cardiac potential signal performed by a personal computer.

If the second period computing module 40 has detected periodicity in peak times detected by the second peak time detection module 39 (Y at S10), the process will proceed to the step S11 in the last part of the flowchart shown in FIG. 15.

The average period comparison module 47 in the fetal heart rate discrimination module 42 acquires, as reference input, the average period acquired by the second average period computing module 41 and an average period of the maternal heart rate signal acquired by the first average period computing module 36, so as to perform comparison (S11). If the average period comparison module 47 has detected a signal of which the period and the average period of the maternal heart rate signal acquired by the first average period computing module 36 have a difference therebetween greater than or equal to a predetermined reference value, it is determined that the detection has been successfully performed. If the average period comparison module 47 has failed to perform the detection successfully (N at S11), the phase comparison module 48 will compare the phase of a peak time of a signal judged to be periodic by the second period computing module 40 and the phase of a peak time of the maternal heart rate signal (S12).

If the difference between the phase of a peak time of a signal judged to be periodic by the second period computing module 40 and the phase of a peak time of the maternal heart rate signal is a predetermined reference phase difference or more, it is determined that the phase comparison module 48 has performed the detection successfully. If the phase comparison module 48 has successfully performed a detection (Y at S13) or if the average period comparison module 47 has successfully performed a detection (Y at S11), the display control module 45 will display the discrimination result on the display 46 (S14).

If the phase comparison module 48 has also failed to perform the detection successfully (N at S13) and if a predetermined period of time set for the discrimination of a fetal heart rate signal for one frame has elapsed, i.e., time is up (Y at S15), the process will return to the step S1 in FIG. 13 and processing for the next frame data will be started. If the predetermined period of time has not elapsed yet (N at S15), the process will return to the step S6 in FIG. 14 and continue from the presumption of a separating matrix.

If the analysis of the data stored in the main memory 31 has not been finished after the display control module 45 displays the discrimination result on the display 46 (N at S16), the process will return to the step S8 in FIG. 14 and continue. In this case, the separating matrix already obtained will be reused. Accordingly, the time for presuming a separating matrix can be eliminated, improving the computation speed. When the analysis of the data stored in the main memory 31 is finished or when the user explicitly selects the termination of the process (Y at S16), the process of this flowchart terminates.

Next, independent component analysis will be briefly described. Independent component analysis (ICA) is a kind of multivariate analyses and suitable for data analysis when there are a number of signal sources and measurements are made in multiple points. Inside the body of a pregnant woman, there are a variety of independent cardiac potential signals S as the signal sources.

[Math. 4]

$$S = \begin{pmatrix} S_1(t) \\ S_2(t) \\ S_3(t) \\ \vdots \\ S_n(t) \end{pmatrix}$$

It is assumed here that $S_1(t)$ is a maternal cardiac potential signal and $S_2(t)$ is a fetal cardiac potential signal, for example. When there are n electrodes for detecting electric potentials on the abdomen of a pregnant woman, observed signals Y from the electrodes are expressed as follows.

[Math. 5]

$$Y = \begin{pmatrix} Y_1(t) \\ Y_2(t) \\ Y_3(t) \\ \vdots \\ Y_n(t) \end{pmatrix}$$

The fetal cardiac potential signal $S2(t)$ is included in small quantities in the respective signals $Y1(t)$-$Yn(t)$ from the electrodes. If it is assumed that a matrix C shown below is related to how much the fetal cardiac potential signal is included, it can be construed that the relationship of $Y=C \cdot S$ is established.

[Math. 6]

$$C = \begin{pmatrix} C_{11} & C_{12} & \ldots & C_{1n} \\ C_{21} & C_{22} & \ldots & C_{2n} \\ \vdots & \vdots & \vdots & \vdots \\ C_{n1} & C_{n2} & \ldots & C_{nn} \end{pmatrix}$$

Accordingly, by obtaining a separating matrix $C^{-1}$, which satisfies the equation $S=C^{-1} \cdot Y$, the maternal cardiac potential signal $S1(t)$ and the fetal cardiac potential signal $S2(t)$ can be acquired based on the electrode potentials. In other words, if the separating matrix $C^{-1}$ is appropriately provided, the maternal and fetal cardiac potential signals will be acquired according to the equation $S=C^{-1} \cdot Y$. Although the detailed description is omitted as independent component analysis is a known method, a separating matrix is converged using a given evaluation function so that an appropriate solution can be obtained.

Figure 16:
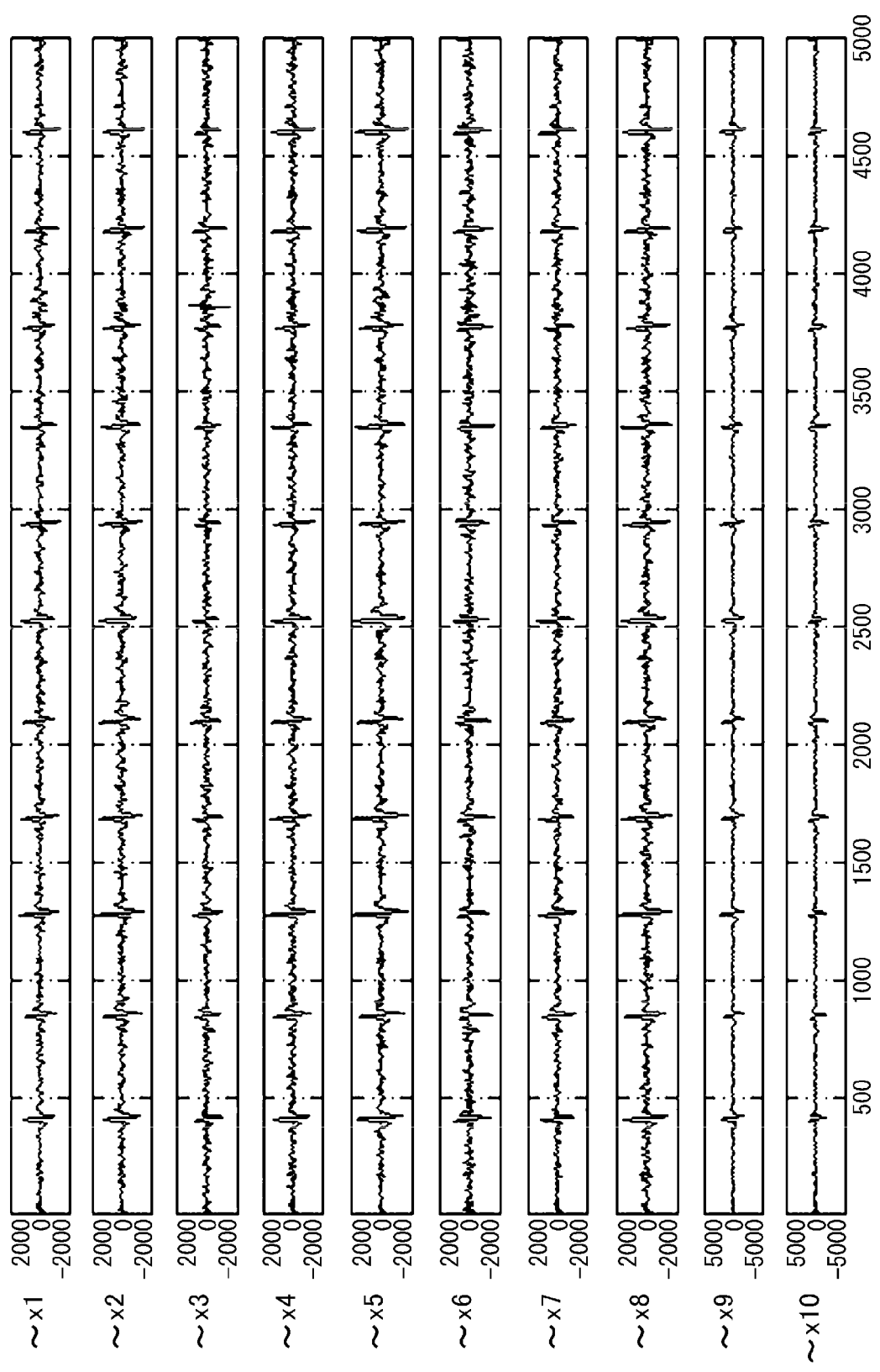
FIG. 16 shows graphs that each illustrate an analog waveform representing a waveform obtained after a filtering process is performed on received signals, where the horizontal axis represents time, and the vertical axis represents signal amplitude based on the electric potential detected at each electrode.
Figure 17:
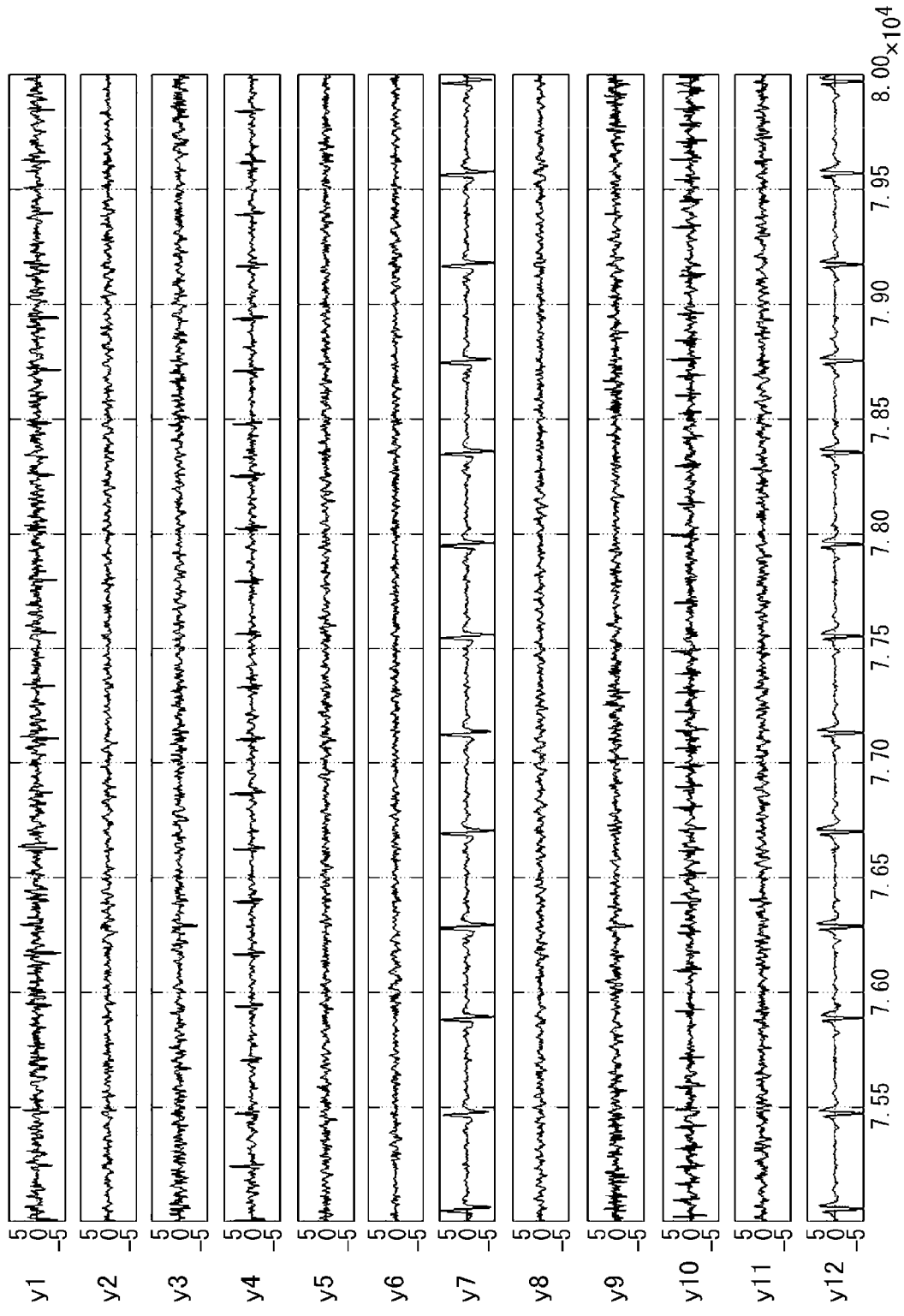
FIG. 17 shows graphs that each illustrate a waveform obtained as a result of independent component analysis.

FIG. 16 shows graphs that each illustrate an analog waveform representing a waveform obtained after processing received signals (hereinafter, referred to as original signals) using a bandpass filter in the PC 20 so as to eliminate noise at a frequency outside the band. In each diagram in FIG. 16, the vertical axis represents signal amplitude based on the electric potential detected at each electrode, and the horizontal axis represents the sampling number. In the example shown in each diagram in FIG. 16, the sampling interval is 2 milliseconds. Since the example of each diagram shows data for 5000 samples, it corresponds to data for 10 seconds, or 2 frames. Although FIG. 16 shows waveforms for 10 channels, waveforms for 12 channels corresponding to the electrodes 1-12 are actually obtained (FIG. 17 shows waveforms for 12 channels). In FIG. 16, periodic potential signals are found in the waveforms of many channels. Large amplitude appearing periodically is derived from the maternal heartbeats.

Although there are differences in level among the waveforms, a maternal cardiac potential signal can be found in each of the signal waveforms shown in FIG. 16. However, it is more preferable that a period is detected based on a signal from an electrode positioned along the vector axis of lead II in the bipolar lead, which is a lead system for electrocardiogram.

FIG. 17 shows graphs that each illustrate a waveform obtained as a result of independent component analysis. As with FIG. 16, each diagram in FIG. 17 shows data for 2 frames. Besides a maternal cardiac potential signal, a fetal cardiac potential signal is also separated and extracted as a result of independent component analysis, and such a fetal cardiac potential signal, which is distinctly different in period from the maternal cardiac potential signal, is found in the fourth top waveform of channel y4. Meanwhile, the maternal cardiac potential signal can be clearly found in each of the waveforms of channels y7 and y12. The PC 20 identifies the potential signal of channel y4 as a fetal cardiac potential signal through the processing described later.

FIG. 17 shows an example in which the analysis results are obtained relatively clearly. Since such analysis results cannot always be obtained, there are cases where a fetal cardiac potential signal can be discriminated by the processing described later and where it cannot be discriminated thereby.

With the fetal cardiac potential signal discriminating apparatus configured as described above, a pregnant woman basically only needs to place the electrodes on her body, and other sensors including an ultrasonic sensor are not required. Also, by focusing on a difference in period between maternal and fetal cardiac potential signals, a fetal cardiac potential signal can be certainly discriminated based on independent component analysis.

Thus, a fetal cardiac potential signal can be discriminated simply and certainly.

Although calculation in independent component analysis has been described above on the premise that the separating matrix is converged so that an appropriate solution can be obtained, there may actually be a case where the separating matrix cannot be converged to obtain an appropriate solution within a predetermined period of time. In such a case, it may be determined as a timeout, so that the analysis currently performed is stopped and shifted to the independent component analysis for the next frame. Naturally, it is concluded in this case that a fetal cardiac potential signal cannot be discriminated for the current frame within the predetermined period of time.

<<Outline of the Pregnancy Monitoring System>>

In FIG. 7, the PC 20 transmits, besides information on a discriminated fetal cardiac potential signal, a signal to be subjected to independent component analysis or other information acquired from a pregnant woman, to the server 22 via the Internet connection 21. Upon reception of the information, the server 22 sends an e-mail, for example, to call attention to the pregnant woman's doctor. The doctor who has received the notification can check the transmitted information using the PC 23 for doctors. If there is a problem in the fetal or maternal heart rate or the like, the doctor will give guidance to the pregnant woman, such as prompting a visit to the hospital. In this way, a pregnant woman can receive appropriate guidance from the doctor while staying at home, so that a monitoring system for safely supporting a pregnant woman until her delivery can be constructed.

Although the PC 20 is used as an information processor for discriminating a fetal cardiac potential signal in the above embodiment, such a function may be implemented by the server 22 or the PC 23 for doctors. If the server 22 or the PC 23 for doctors has high throughput, the accuracy of the separation and extraction process can be improved by allowing the server 22 or the PC 23 to perform independent component analysis a number of times. Instead of the PC 20, a terminal dedicated to input and display functions, such as a PDA (personal digital assistance), can also be used. In this case, the server 22 or the PC 23 for doctors serves as the information processor for discriminating a fetal cardiac potential signal.

In principle, the function of the information processor for discriminating a fetal cardiac potential signal may be provided within the transmission unit 100s. Also, another system configuration may be available in which information is directly transmitted from the transmission unit 100s to the server 22 via long-distance wireless communication, without dependence on a personal computer in a pregnant woman's house.

Namely, various variations can be provided for the place where an information processor provided with the function to discriminate a fetal cardiac potential signal is installed.

(Modification)

Figure 18:
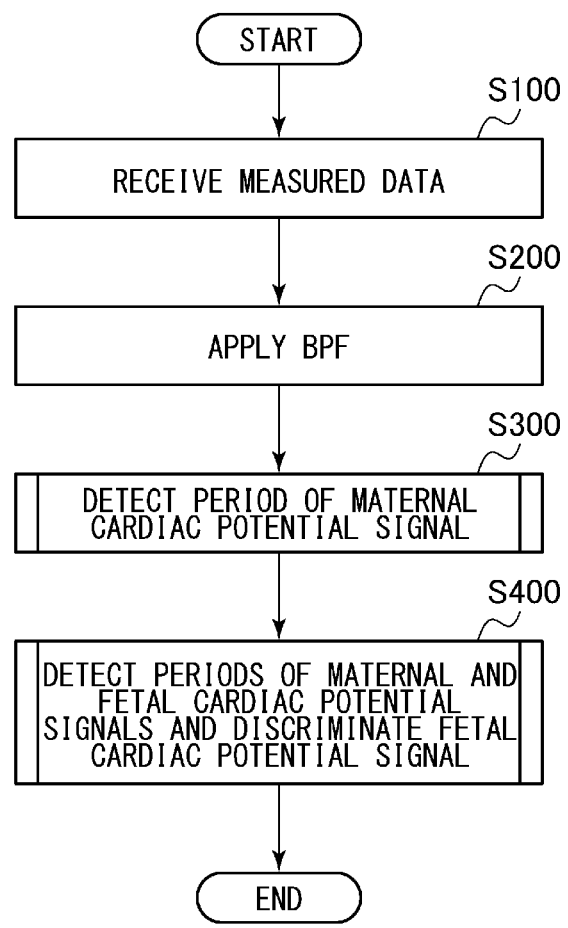
FIG. 18 is a flowchart that shows illustrative processing for discriminating a fetal cardiac potential signal according to a modification of the present invention.

FIG. 18 is a flowchart that shows illustrative processing for discriminating a fetal cardiac potential signal according to a modification of the present invention. In the step S100, the PC 20 receives, from the measuring apparatus 100, biopotential signals (information) derived from both a mother and a fetus for a certain period (step S100) and stores the signals.

The PC 20 performs the detection of a period of a maternal cardiac potential signal (step S300) and also performs the detection of periods of maternal and fetal cardiac potential signals and the discrimination of a fetal cardiac potential signal (step S400). Although the steps S300 and S400 may be performed simultaneously in parallel, the detection of a period of a maternal cardiac potential signal at the step S300 need be completed before the discrimination of a fetal cardiac potential signal is performed.

A waveform after a filtering process is divided into multiple frames (periods) that each have a certain period of time, and the processing of the step S400 is performed for each of the frames.

Figure 19:
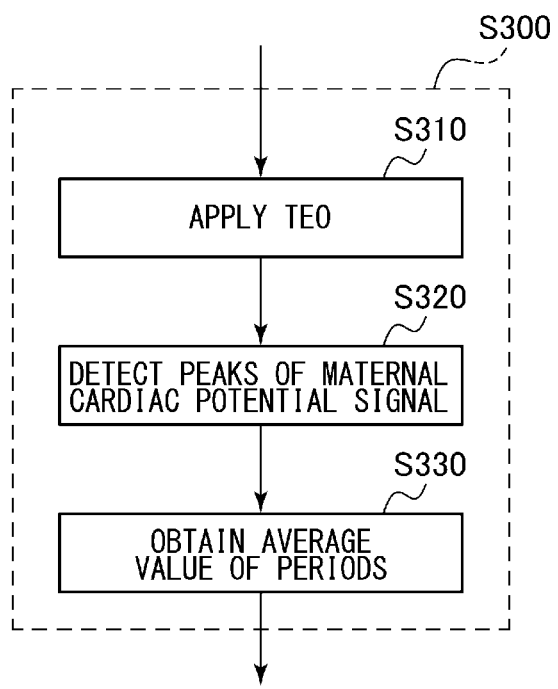
FIG. 19 is a flowchart that shows an example of specific processing for detecting a period of a maternal cardiac potential signal according to the modification of the present invention.

FIG. 19 is a flowchart that shows an example of specific processing for the detection of a period of a maternal cardiac potential signal (step S300) mentioned above. First, the PC 20 applies the Teager energy operator (TEO) to signals after the filtering process so as to improve the S/N ratio in a signal waveform (step S310).

The PC 20 then sets a threshold and detects peaks of a maternal cardiac potential signal exceeding the threshold (step S320). It is preferable to change the threshold according to expected peak times rather than setting it to a certain value. If a lower threshold is set, noise or other components are also likely to be mistakenly detected besides peaks of a maternal cardiac potential signal actually required; on the other hand, if a higher threshold is set, the detection of an actually required peak may fail. However, by appropriately changing the threshold according to expected peak times, required signals (peaks) can be detected more certainly while eliminating unnecessary signals. Peak times can be predicted based on empirical values of a maternal cardiac potential signal. Based on such peak detection, the PC 20 acquires and stores periods, and then defines an average value of multiple periods thus stored as the period of the maternal cardiac potential signal (step S330).

Figure 20:
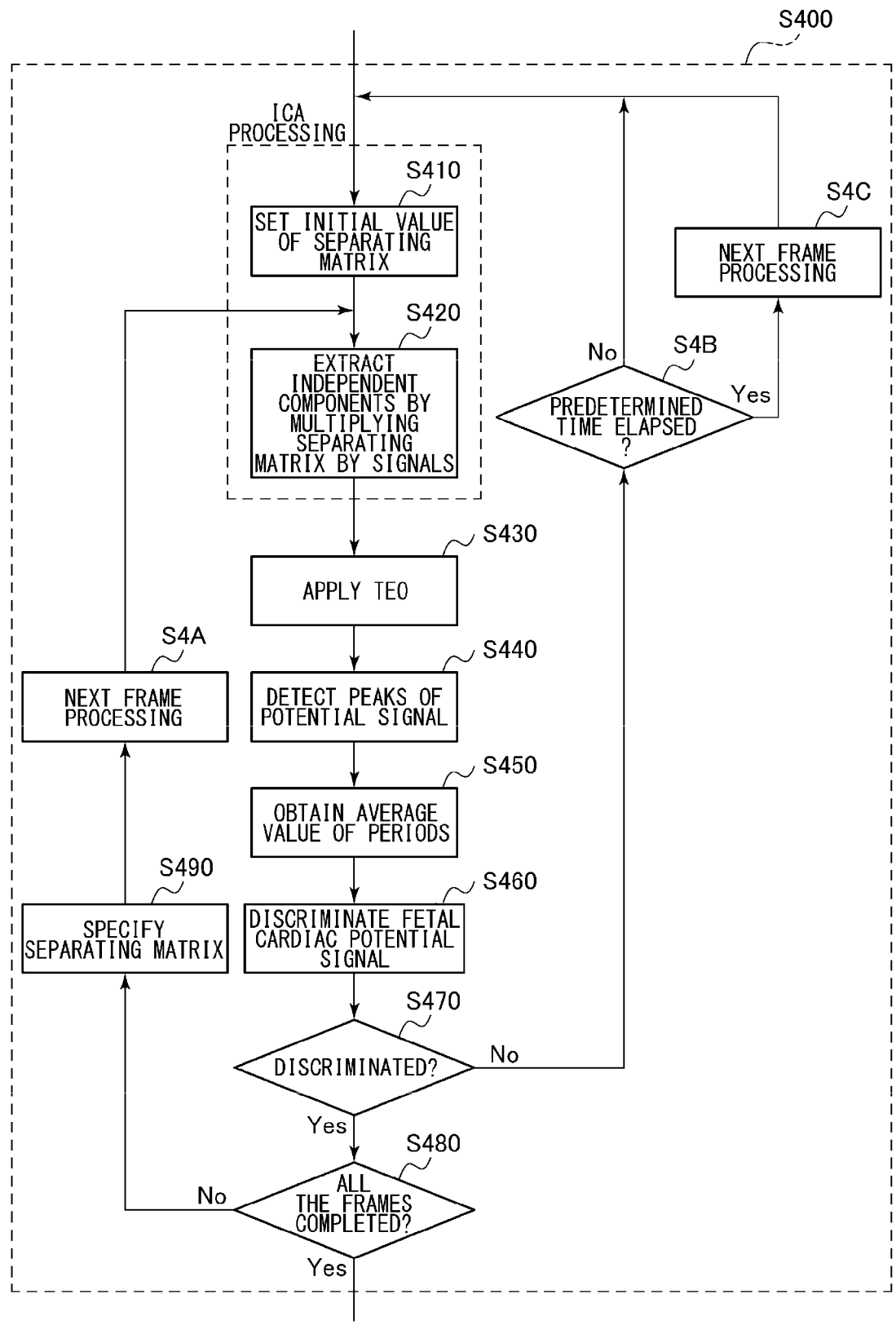
FIG. 20 is a flowchart that shows processing for detecting periods of a maternal cardiac potential signal and a fetal cardiac potential signal and for discriminating a fetal cardiac potential signal according to the modification of the present invention.

Subsequently, the PC 20 performs processing of independent component analysis in the flowchart shown in FIG. 20 (steps S410 and S420). More specifically, the PC 20 sets an initial value of a separating matrix using a random number (step S410). The PC 20 then multiplies the separating matrix by signals after the filtering process (corresponding to the calculation of $S=C^{-1} \cdot Y$ stated previously) (step S420) and extracts independent components to be candidates of maternal and fetal signals.

Referring back to FIG. 20, the PC 20 applies the Teager energy operator to extracted signals so as to improve the S/N ratio in a signal waveform (step S430). As described previously, the method using the Teager energy operator is significantly effective when the power of a cardiac potential signal is greater than the power of noise. Therefore, the S/N ratio is improved in the waveforms of channels y4, y7, and y12 in FIG. 17, which each show a large signal with relatively small noise, whereas the signals of the other channels do not have significant improvements in the S/N ratio.

Next, the PC 20 sets a threshold and detects peaks of a signal waveform exceeding the threshold (step S440). As described previously, it is preferable to change the threshold according to expected peak times rather than setting it to a certain value. Peak times can be predicted based on empirical values of maternal and fetal cardiac potential signals. When periodic peaks are detected in a signal of a channel, the PC 20 obtains and stores periods of the peaks. In this processing, the subject signals can be narrowed down to the signals of channels y4, y7, and y12 having improved S/N ratio before periods of peak times of the signals are acquired. The PC 20 also obtains an average value of multiple periods thus stored (step S450). In this case, the period of the signal of channel y7 and the period of the signal of channel y12 are identical with each other because the signal source thereof is the same (maternal heartbeats). On the other hand, the period of the signal of channel y7 (or y12) and the period of the signal of channel y4 are greatly different from each other.

Through the above processing, there can be acquired a period τm of a maternal cardiac potential signal based on a signal obtained by performing a filtering process on the original signals, a period τm' of a maternal cardiac potential signal and a period τf of a fetal cardiac potential signal based on the signals obtained by performing independent component analysis on the signals after the filtering process. Generally, the periods τm and τm' of the maternal cardiac potential signal agree well with each other only with differences in decimal places. On the other hand, since a fetus generally has a far higher heart rate than a mother, a period clearly much different from τm and τm' is thought to be the period τf of the fetal cardiac potential signal. Accordingly, the PC 20 determines that the signal of channel y4 is the fetal cardiac potential signal (step S460).

The signal waveform identified as a fetal cardiac potential signal is displayed on the screen of the PC 20. Alternatively, all of or part (such as channels y4 and y7) of the signal waveforms of the respective channels as shown in FIG. 17 may be displayed. Further, a heart rate obtained by performing back calculation from the period of the fetal cardiac potential signal or maternal cardiac potential signal may be displayed digitally or graphically. Accordingly, a pregnant woman can check the fetal heart rate or a change thereof while staying at home.

Meanwhile, there may be a case where the fetal cardiac potential signal cannot be discriminated depending on the result of the independent component analysis. Accordingly, the PC 20 determines whether or not the discrimination could have been made (step S470). If the discrimination has failed, the PC 20 will determine whether or not a predetermined period of time has elapsed after the start of the independent component analysis (step S4B). Then, if it is within the predetermined period of time, the PC 20 will continuously perform the independent component analysis and repeat the processes of the steps S410-S470. If the predetermined period of time has elapsed while the discrimination has failed, the PC 20 will abandon the process for the current frame and shift to processing for the next frame (step S4C). In this way, when the discrimination cannot be made within a predetermined period of time, the process can be reasonably continued by spending no more time on the current process and performing independent component analysis for the next period.

If the discrimination could have been made, on the other hand, it will be determined whether or not the processing (steps S410-S460) has been completed for all the frames (step S480), the separating matrix will be specified (step S490), and the process will be shifted to processing for the next frame (step S4A). In this case, since the specified separating matrix will be used as the initial value in the next independent component analysis, the process will be started from the step S420. Accordingly, the time required for the independent component analysis can be reduced thereafter. If the processing for all the frames has been completed (Yes at step S480), the processing of the step S400 (FIG. 20) will be terminated. Continuously, the processing shown in FIG. 20 will be performed repeatedly.

<<Other Modifications>>

Although a fetal cardiac potential signal is identified based on the period in the above embodiment, there may be an extremely rare case where a maternal cardiac potential signal and a fetal cardiac potential signal have no difference in period. Accordingly, if the PC 20 has failed the discrimination of a fetal cardiac potential signal, peak times may be detected from the waveforms of candidates of the maternal cardiac potential signal and fetal cardiac potential signal so as to compare the phases. More specifically, in this case, the phase of a maternal cardiac potential signal detected in a different way from the independent component analysis and the phase of a candidate potential signal of each of the maternal cardiac potential signal and fetal cardiac potential signal after the independent component analysis are compared, and a potential signal of which the phase is greatly different may be identified as a fetal cardiac potential signal. Accordingly, even in the extremely rare case where a difference in period is not clear, a fetal cardiac potential signal can be detected using a difference in phase.

From the beginning, a fetal cardiac potential signal may be detected based on the phase, instead of the period. In this case, the information processor is configured to detect the phase of a certain part (the peak of an R wave, for example) of a maternal cardiac potential signal from the waveforms of biopotential signals, perform independent component analysis on biopotential signals to obtain multiple potential signals having phases different from each other, compare the phase of a certain part of each of the multiple potential signals with the phase of the maternal cardiac potential signal, and identify a potential signal having a greatly different phase as a fetal cardiac potential signal.

The modifications of the embodiment of the present invention described above can be identified by the following description.

(1) A fetal cardiac potential signal discriminating apparatus of the present invention comprises: a measuring apparatus configured to acquire, from multiple electrodes placed on the body of a pregnant woman, biopotential signals derived from both the mother and the fetus; and an information processor configured to detect a period of a maternal cardiac potential signal from the waveforms of the biopotential signals, perform independent component analysis (ICA) on the biopotential signals to obtain multiple potential signals having periods different from each other, compare the periods of the multiple potential signals with the period of the maternal cardiac potential signal, and identify a potential signal having a greatly different period as a fetal cardiac potential signal.

In the fetal cardiac potential signal discriminating apparatus configured as described above, the measuring apparatus acquires biopotential signals derived from both the mother and the fetus. From the waveforms of the biopotential signals, the information processor detects a period of a maternal cardiac potential signal. The information processor also performs independent component analysis on the biopotential signals to obtain multiple potential signals having periods different from each other. The multiple potential signals include a maternal cardiac potential signal and a fetal cardiac potential signal. By comparing, in period, such potential signals with a maternal cardiac potential signal detected in a different way from the independent component analysis, a potential signal having a greatly different period can be identified as a fetal cardiac potential signal.

(2) In the fetal cardiac potential signal discriminating apparatus described in (1), the information processor may change a threshold used in a comparison for detecting periodic peaks appearing in a potential signal, according to expected peak times.

If a lower threshold is set, noise or other components are also likely to be mistakenly detected besides signals actually required; on the other hand, if a higher threshold is set, the detection of an actually required signal may fail. However, by appropriately changing the threshold according to expected peak times, required signals (peaks) can be detected more certainly while eliminating unnecessary signals.

(3) In the fetal cardiac potential signal discriminating apparatus described in (2), it is preferable that a peak is the peak of an R wave in each of a maternal cardiac potential signal and a fetal cardiac potential signal.

Since it has a significant peak with a greater value, an R wave can be easily detected.

(4) In the fetal cardiac potential signal discriminating apparatus described in (1) or (2), it is preferable that the information processor applies the Teager energy operator to biopotential signals or potential signals obtained by performing independent component analysis on the biopotential signals.

In this case, the S/N ratio is improved in a signal waveform, so that the period of the potential signal can be easily acquired.

(5) In the fetal cardiac potential signal discriminating apparatus described in (1), when a fetal cardiac potential signal cannot be discriminated by the comparison of the periods, the information processor may identify a potential signal having a phase greatly different from that of a maternal cardiac potential signal as a fetal cardiac potential signal.

In this case, even if a potential signal having a greatly different period cannot be clearly detected, a fetal cardiac potential signal can be detected using a difference in phase.

(6) In the fetal cardiac potential signal discriminating apparatus described in (1), it is preferable that, for the presumption of a separating matrix for independent component analysis using a random number, the information processor uses a separating matrix applied when a fetal cardiac potential signal could have been discriminated, as a separating matrix for the next time.

In this case, the time required for the independent component analysis can be reduced thereafter.

(7) In the fetal cardiac potential signal discriminating apparatus described in (1), when a fetal cardiac potential signal cannot be discriminated within a predetermined period of time, the information processor may stop the independent component analysis and perform independent component analysis for the next period.

In this case, when the discrimination cannot be made within a predetermined period of time, the process can be reasonably continued by spending no more time on the current process and performing independent component analysis for the next period.

(8) In the fetal cardiac potential signal discriminating apparatus described in any of (1) through (7), the electrodes may be provided on a maternity girdle, so that, when a pregnant woman wears the maternity girdle, the electrodes can be firmly attached to her abdomen.

In this case, a pregnant woman can easily place the electrodes without someone's help.

(9) A pregnancy monitoring system including the fetal cardiac potential signal discriminating apparatus described in (1) also comprises a server connectable to the measuring apparatus via a communication line, in which the information processor may be configured by at least one of an information processor installed in a pregnant woman's house, the server, and an information processor for doctors connectable to the server.

With such a pregnancy monitoring system, a doctor can check information on the fetal or maternal heart rate and the like via the server, and a pregnant woman can receive appropriate guidance from the doctor while staying at home.

(10) A fetal cardiac potential signal discriminating method of the present invention comprises: acquiring, from multiple electrodes placed on the body of a pregnant woman, biopotential signals derived from both the mother and the fetus; detecting a period of a maternal cardiac potential signal from the waveforms of the biopotential signals; performing independent component analysis on the biopotential signals to obtain multiple potential signals having periods different from each other; and identifying, when the periods of the multiple potential signals are compared to the period of the maternal cardiac potential signal, a potential signal having a greatly different period as a fetal cardiac potential signal.

In the fetal cardiac potential signal discriminating method described above, biopotential signals derived from both the mother and the fetus are acquired, and a period of a maternal cardiac potential signal is detected from the waveforms of the biopotential signals. Also, independent component analysis is performed on the biopotential signals to obtain multiple potential signals having periods different from each other. The multiple potential signals include a maternal cardiac potential signal and a fetal cardiac potential signal. By comparing, in period, such potential signals with a maternal cardiac potential signal detected in a different way from the independent component analysis, a potential signal having a greatly different period can be identified as a fetal cardiac potential signal.

(11) The fetal cardiac potential signal discriminating apparatus of the present invention may be an apparatus comprising: a measuring apparatus configured to acquire, from multiple electrodes placed on the body of a pregnant woman, biopotential signals derived from both the mother and the fetus; and an information processor configured to detect the phase of a certain part of a maternal cardiac potential signal from the waveforms of the biopotential signals, perform independent component analysis on the biopotential signals to obtain multiple potential signals having phases different from each other, compare the phase of the certain part of each of the multiple potential signals with the phase of the maternal cardiac potential signal, and identify a potential signal having a greatly different phase as a fetal cardiac potential signal.

In the fetal cardiac potential signal discriminating apparatus configured as described above, the measuring apparatus acquires biopotential signals derived from both the mother and the fetus. From the waveforms of the biopotential signals, the information processor detects the phase of a certain part of a maternal cardiac potential signal. The information processor also performs independent component analysis on the biopotential signals to obtain multiple potential signals having phases different from each other. The multiple potential signals include a maternal cardiac potential signal and a fetal cardiac potential signal. By comparing, in phase, such potential signals with a maternal cardiac potential signal detected in a different way from the independent component analysis, a potential signal having a greatly different phase can be identified as a fetal cardiac potential signal.

Instead of the PC 20 in the above description, a user's portable information terminal, such as a smartphone, may perform information processing and display the result. In such a case, bioelectric potentials can also be analyzed at a place other than the place where the PC 20 is installed. Also, this case provides another advantage that the analysis result can be immediately checked while measuring bioelectric potentials.

What is claimed is:

1. A non-transitory computer-readable recording medium storing a computer program for extracting a fetal cardiac potential signal, the computer program comprising:
   a selecting module configured to select, from among a plurality of biopotential signals, a biopotential signal containing a high proportion of a maternal cardiac potential signal component;
   an independent component analysis module configured to perform independent component analysis on the plurality of biopotential signals;
   a periodic signal detection module configured to detect, as a first peak time signal, a signal having periodic peaks from a biopotential signal selected by the selecting module and to detect, as second peak time signals, one or more signals having periodic peaks among signals output from the independent component analysis module wherein the periodic signal detection module includes:
   a module configured to acquire an energy signal of the selected biopotential signal;
   a module configured to acquire a moving average signal of the energy signal based on a predetermined window width; and
   a module configured to detect a peak from a signal in a region having a greater value than the moving average signal in the energy signal;
   an output signal selecting module configured to acquire the first peak time signal as reference input and also acquire the one or more second peak time signals as comparison input, so as to select from among the one or more second peak time signals a signal having peak times different from those of the first peak time signal; and
   a module configured to output a signal selected by the output signal selecting module,
   wherein the periodic signal detection module judges, when the variance of intervals between detected peaks is a predetermined reference variance value or less, an output signal having such peak intervals to be a periodic peak time signal.

2. The non-transitory computer-readable recording medium of claim 1, wherein the output signal selecting module includes:
   a module configured to acquire an average value of peak intervals of the first peak time signal as a first average value;
   a module configured to acquire an average value of peak intervals of a second peak time signal as a second average value; and
   a module configured to select, when a difference between the second average value of a second peak time signal and the first average value is greater than or equal to a predetermined reference value, the second peak time signal as a signal having peak times different from those of the first peak time signal.

3. A pregnancy monitoring system, comprising:
a maternity girdle having a plurality of electrodes provided thereon for acquiring a plurality of biopotential signals derived from both a mother and a fetus; and
a portable information processor configured to perform the computer program stored in the non-transitory computer-readable recording medium of claim 1 and capable of being carried by a pregnant woman wearing the maternity girdle, wherein
the portable information processor displays an output signal selected by the output signal selecting module.

4. A pregnancy monitoring system, comprising:
a maternity girdle having a plurality of electrodes provided thereon for acquiring a plurality of biopotential signals derived from both a mother and a fetus; and
an information processor configured to perform the computer program stored in the non-transitory computer-readable recording medium of claim 1 and installed in the house of a pregnant woman wearing the maternity girdle; and
a server connected to the information processor via a communication line.

5. A non-transitory computer-readable recording medium storing a computer program for extracting a fetal cardiac potential signal, the computer program comprising:
a selecting module configured to select, from among a plurality of biopotential signals, a biopotential signal containing a high proportion of a maternal cardiac potential signal component;
an independent component analysis module configured to perform independent component analysis on the plurality of biopotential signals;
a periodic signal detection module configured to detect, as a first peak time signal, a signal having periodic peaks from a biopotential signal selected by the selecting module and to detect, as second peak time signals, one or more signals having periodic peaks among signals output from the independent component analysis module an output signal selecting module configured to acquire the first peak time signal as reference input and also acquire the one or more second peak time signals as comparison input, so as to select from among the one or more second peak time signals a signal having peak times different from those of the first peak time signal; and
a module configured to output a signal selected by the output signal selecting module,
wherein the output signal selecting module further includes a module configured to select, when there is no signal of which the second average value and the first average value have a difference therebetween greater than or equal to a predetermined reference value and when a difference between the phase of a peak time of a second peak time signal and the phase of a peak time of the first peak time signal is greater than or equal to a predetermined reference phase difference, the second peak time signal as a signal having peak times different from those of the first peak time signal.

6. A non-transitory computer-readable recording medium storing a computer program for extracting a fetal cardiac potential signal, the computer program comprising:
a selecting module configured to select, from among a plurality of biopotential signals, a biopotential signal containing a high proportion of a maternal cardiac potential signal component;
an independent component analysis module configured to perform independent component analysis on the plurality of biopotential signals;
a periodic signal detection module configured to detect, as a first peak time signal, a signal having periodic peaks from a biopotential signal selected by the selecting module and to detect, as second peak time signals, one or more signals having periodic peaks among signals output from the independent component analysis module an output signal selecting module configured to acquire the first peak time signal as reference input and also acquire the one or more second peak time signals as comparison input, so as to select from among the one or more second peak time signals a signal having peak times different from those of the first peak time signal; and
a module configured to output a signal selected by the output signal selecting module,
wherein the independent component analysis module includes:
a separating matrix acquisition module configured to compute a separating matrix used to separate a plurality of biopotential signals into independent components; and
a multiplication module configured to multiply a plurality of biopotential signals by the separating matrix to acquire an output signal, and
wherein, when the separating matrix is known, the independent component analysis module multiplies the plurality of biopotential signals by the known separating matrix to acquire an output signal, without computing the separating matrix.

7. A fetal cardiac potential signal discriminating apparatus, comprising:
a measuring apparatus configured to acquire, from a plurality of electrodes placed on the body of a pregnant woman, biopotential signals derived from both a mother and a fetus; and
an information processor configured to:
select, from among a plurality of biopotential signals, a biopotential signal containing a high proportion of a maternal cardiac potential signal component;
perform independent component analysis on the plurality of biopotential signals;
detect, as a maternal cardiac signal, a signal having periodic peaks from a biopotential signal selected and to detect, as second peak time signals, one or more signals having periodic peaks among signals output;
acquire the maternal cardiac signal as reference input and also acquire the one or more second peak time signals as comparison input, so as to select, as a fetal cardiac potential signal, from among the one or more second peak time signals a signal having peak times different from those of the maternal cardiac signal; and
output the fetal cardiac potential signal,
wherein the detection includes:
acquiring an energy signal of the selected biopotential signal;
acquiring a moving average signal of the energy signal based on a predetermined window width; and
detecting a peak from a signal in a region having a greater value than the moving average signal in the energy signal; and
judging when the variance of intervals between detected peaks is a predetermined reference variance value or less, an output signal having such peak intervals to be a periodic peak time signal.

* * * * *